(12) United States Patent
Kralovec

(10) Patent No.: US 6,551,596 B2
(45) Date of Patent: Apr. 22, 2003

(54) FRACTIONS OF CHLORELLA EXTRACT CONTAINING POLYSACCHARIDE HAVING IMMUNOMODULATING PROPERTIES

(75) Inventor: Jaroslav A. Kralovec, Halifax (CA)

(73) Assignee: Ocean Nutrition Canada Limited, Halifax (CA)

( * ) Notice: Subject to any disclaimer, the term of this patent is extended or adjusted under 35 U.S.C. 154(b) by 0 days.

(21) Appl. No.: 09/925,953

(22) Filed: Aug. 10, 2001

(65) Prior Publication Data

US 2002/0031524 A1 Mar. 14, 2002

Related U.S. Application Data

(60) Provisional application No. 60/224,014, filed on Aug. 10, 2000.

(51) Int. Cl.$^7$ .................. A61K 35/80; A61K 47/00; C12N 1/12
(52) U.S. Cl. ............. 424/195.17; 424/439; 435/257.3; 435/946
(58) Field of Search ................... 424/184.1, 193.1, 424/274.1, 276.1, 278.1, 93.7, 195.17, 93.1, 439; 435/257.3, 946

(56) References Cited

U.S. PATENT DOCUMENTS

| | | | |
|---|---|---|---|
| 3,462,412 A | 8/1969 | Yamada et al. | 260/209 |
| 4,143,162 A | 3/1979 | Tanaka | 426/89 |
| 4,533,548 A | 8/1985 | Umezawa | 514/54 |
| 4,786,496 A | 11/1988 | Watanabe et al. | 424/195.1 |
| 4,831,020 A | 5/1989 | Watanabe et al. | 514/54 |
| 4,931,291 A * | 6/1990 | Kojima et al. | 426/2 |
| 5,780,096 A | 7/1998 | Tanaka | 426/655 |
| 5,871,952 A | 2/1999 | Ghirardi et al. | 435/34 |
| 6,022,573 A * | 2/2000 | Hagiwara | 426/270 |
| 6,027,900 A | 2/2000 | Allnutt et al. | 435/6 |
| 6,183,968 B1 * | 2/2001 | Bandman et al. | 435/6 |

FOREIGN PATENT DOCUMENTS

| | | |
|---|---|---|
| CA | 2270106 | 4/1999 |
| EP | 0295956 | 12/1988 |
| GB | 1141821 | 2/1969 |
| JP | 7779016 | 7/1977 |
| JP | 57014533 A | 1/1982 |
| JP | 58015920 | 1/1983 |
| JP | 61078729 A | 4/1986 |
| JP | 61096992 | 5/1986 |
| JP | 05039894 | 9/1994 |
| JP | 06248003 | 9/1994 |
| WO | WO0204000 | 1/2002 |

OTHER PUBLICATIONS

XP002199857 & JP 44 023343 B *(Yamada H) Abstract; Database WPI Section Ch, Derwent Publications Ltd., London, GB; Class B00, AN 1966–40421F.

XP002199913 & JP 58 015920 A (Chlorella Kogyo KK) Jan. 29, 1983 Abstract; Database WPI Section Ch, Week 198310, Derwent Publications Ltd., London, GB; Class B04, AN 1983–23836K.

Kessler, E. "Phycotalk" 1989, 1:141–153 V. Rastogi Publ., New Delhi, India.

Lee, Robert E. "Phycology" $2^{nd}$ edition; 1989, p. 281; Cambridge University Press.

Tanaka et al. Immunopharmacol. Immunotoxicol., 1990, 12(2):277–291 (abstract).

Tanaka et al. Cancer Immunol. Immunother., Feb. 1998, 45(6):313–320 (abstract).

Hasegawa et al. Int. J. Immunopharmacol., 1990, 12(8):883–891 (abstract).

Neveu et al. Experientia, Dec. 15, 1978, 34(12):1644–1645 (abstract).

Vermeil and Morin CR Seances Soc. Biol. Fil., Oct. 1976, 170(3):646–649 (abstract in English).

Miyazawa et al. J. Ethnopharmacol., Dec. 1988, 24(2–3):135–146 (abstract).

Umezawa et al., An acidic polysaccharide, Chlon A, from *Chlorella pyrenoidosa*. I. Physiochemical and biological properties Chemotherapy, Sep. 1982, 30(9):1041–1046 (abstract in English; parts of article in English).

Komiyama et al. Chemotherapy, 1986, 34:302–307 (English short description).

White and Barber, Biochimica Biophysica Acta, 1972, 264:117–128.

Kojima et al. J. Retic. Soc., 1973, 14:192–208.

Mizuno et al. Bull. Fac. Agr. Shizuoka Univ. (Shizuoka Daigaku Nogakubu Kenkyu Hokoku), 1980, 30:51–59 (abstract in English).

(List continued on next page.)

*Primary Examiner*—David M. Naff
*Assistant Examiner*—Deborah K. Ware

(57) ABSTRACT

Chlorella fractionated extracts containing high molecular weight Chlorella polysaccharide and polysaccharide complexes show immune modulatory, specifically immune stimulatory activity. The fractionated extracts are obtained by size fractionation of an extract of Chlorella and selecting fractions containing high molecular weight polysaccharides and polysaccharide complexes of about $1 \times 10^4$ Da to about $1 \times 10^7$ Da. A fraction of about $4 \times 10^6$ Da to about $1 \times 10^7$ Da is preferably obtained by size fractionation. The polysaccharide and polysaccharide complexes contain glucose and any combination of: galactose, rhamnose, mannose and arabinose, as well as N-acetyl glucosamine and N-acetyl galactosamine. The extracts may be treated with pronase, DNAse, RNAse and proteases to remove unassociated nucleic acids, ribonucleic acids and proteins. The extracts may also undergo treatment to effect cleavage of specific glycosidic linkages, the linkages being defined by their susceptibility to cleavage by amylase, amyloglucosidase, cellulase or neuraminidase. Chlorella extracts may be administered to a mammal to increase proliferation of splenocytes and increase production of cytokines such as IL-6, IL-10, INF-γ and TNF-α. They may be used as a supplement to a vaccination regimen.

25 Claims, 10 Drawing Sheets

OTHER PUBLICATIONS

Ukai et al. Ann. Proc. Gifu Pharm. Univ. (Gifu Yakka Daigaku Kiyo), 1990, 39:44–48 (abstract in English).

Chu et al., "Polysaccharide composition of five algal species used as food for larvae of the American oyster, *Crassostrea virginica*", Aquaculture (1982), 29(3–4), 241–52 (abstract).

World Catalogue of Algae, 2$^{nd}$ Edition, pp. 58–66, 68, 69, 72–74; Miyachi et al. (Eds); 1989; Japan Scientific Societies Press.

www.taiwanchlorella.com/product–3.htm.

http://www.uku.fi/laitokset/anat/PG/c_method.htm.

Ogawa et al., "Isolation and Identification of 3–O–Methyl–D–galactose as a Constituent of Neutral Polysaccharide of *Chlorella vulgaris*", Biosci. Biotech. Biochem., 1997, 58(5):942 and 944.

Komiyama et al., "An acidic polysaccharide Chlon A, from *Chlorella pyrenoidosa*", The Kitasato Institute, pp. 1–6.

Ogawa et al. "Isolation and Identification of 2–O–Methyl–L–rhamnose and 3–O–Methyl–L–rhamnose as Constituents of an Acidic Polysaccharide of *Chlorella vulgaris*", Biosci. Biotech. Biochem., 1997, 61(3):539–540.

Brown and Jeffrey, Biochemical composition of microalgae from the green algal classes Chlorophyceae and Prasinophyceae. L. Amino acids, sugars and pigments, J. Exp. Mar. Biol. Ecol. 161 (1992) 91–113.

Bold and Wynne, "Introduction to the Algae Structure and Reproduction" 2$^{nd}$ edition; p. 142, Prentice–Hall, Inc.

Konishi et al., "Enhanced resistance against *Escherichia coli* infection by subcutaneous administration of the hot–water extract of *Chlorella vulgaris* in cyclophosphamide–treated mice", Cancer Immunol. Immunother., 1990, 32(1):1–7 (abstract).

Terziev et al., "Use of nonspecific agents and vaccination in bronchopneumonia prevention in cattle", Vet Med Nauki, 1983, 20(1):36–9 (abstract in English).

Rotkovska et al., "The radioprotective effects of aqueous extract from chlorococcal freshwater algae (*Chlorella kessleri*) in mice and rats", Strahlenther Onkol, Nov. 1989, 165(11):813–6 (abstract).

Tanaka et al., "Oral administraction of a unicellular green algae, *Chlorella vulgaris*, prevents stress–induced ulcer", Planta Med, Oct. 1997, 63(5):465–6 (abstract).

Hasegawa et al., "Oral administration of hot water extracts of *Chlorella vulgaris* reduces IgE production against milk casein in mice", Int. J. Immunopharmacol., May 1999, 21(5):311–23 (abstract).

Dantas and Queiroz, "Effects of *Chlorella vulgaris* on bone marrow progenitor cells of mice infected with Listeria monocytogenes", Int. J. Imunopharmacol., Aug. 1999, 21(8):499–508 (abstract).

Hasegawa et al., "Hot water extracts of *Chlorella vulgaris* reduce opportunistic infection with Listeria monocytogenes in C57BL/6 mice infected with LP–BM5 murine leukemia viruses", Int. J. Immunopharmacol., Jun. 1995, 17(6):505–12 (abstract).

Hasegawa et al., "Effect of hot water extract of *Chlorella vulgaris* on cytokine expression patterns in mice with murine acquired immunodeficiency syndrome after infection with Listeria monocytogenes", Immunopharmacology, Jan. 1997, 35(3):273–82 (abstract).

Hasegawa et al., "Augmentation of the resistance against Listeria monocytogenes by oral administration of a hot water extract of Chlorella vulgaris in mice", Immunopharmacol. Immunotoxicol., May 1994, 16(2):191–202 (abstract).

Tanaka et al., "A novel glycoprotein obtained from *Chlorella vulgaris* strain CK22 shows antimetastatic immunopotentiation", Cancer Immunol. Immunother., Feb. 1998, 45(6):313–20 (abstract).

Kotrbacek et al., "Increased immune response in broilers after administration of natural food supplements", Vet Med (Praha) 1994, 39(6):321–8 (abstract in English).

Ogawa et al., (1998) "New aldobiuronic acid, 3–O–α–D–Glucopyranuronosyl–L–rhamnopyranose, from an acidic polysaccharide of *Chlorella vulgaris*" Biosci. Biotechnol. Biochem. 62:2030–1 (short description).

Ogawa et al., (1997) "An acidic polysaccharide of *Chlorella vulgaris*" Biosci. Biotechnol. Biochem. 62:2030–, Isolation and identification of 2–O–methyl–L–rhamnose and of 3–O–methy–l–rhamnose of an acidic polysaccharide of *Clorella vulgaris*(short description).

Kapaun et al., (1995) "A chitin–like glycan in the cell wall of a Chlorella sp.(Chlorococcales, Chlorophyceae)" Planta 197(4)577–82 (short description).

Yalcin et al., (1994) "Characterization of the extracellular polyssacharide from freshwater microalgae Chlorella sp." Food Sci. Technol. (short description).

Komiyama et al., (1986) "An acidic polysaccharide, Chlon A, from *Chlorella pyrenoidosa*. II. Antitumor activity and immunological response" Chemotherapy 34:302–7 (short description).

Kojima et al., "Biological activities of Chlorella polysaccharide. I. Extraction of an active polysaccharide from Chlorella cells and its stimulative effect on phagocytic activity of rat reticuloendothelial system", Nippon Nogei Kagaku Kaishi (1972), 46(8), 373–80 (partial abstract).

Mizuno et al., (1980) "Studies on the carbohydrates of Chlorella. III. Fractionation and some biological activities of the Chlorella polysaccharides", Shizuoka Daigaku Nogakubu Kenkyu Hokoku 30:51–9 (short description).

Shino K. (1980) "Cell walls and polysaccharides of Chlorella", New Food Ind. 22:18–32 (short description).

Kojima et al. (1974) "New Chlorella polysaccharide and its accelerating effect on the phagocytic activity of the reticuloendothelial system", Recent Adv RES Res (1974) 13:101–22 (abstract and short description).

Kojima et al., (1973) "Chlorella polysaccharide as a factor stimulating RES (reticuloendothelial system) activity", RES J. Reticuloendothel. Soc. 14(2):192–208 (abstract and short description).

Kojima et al., (1972) "Biological activities of Chlorella polysaccharide. I. Extraction of an active polysaccharide from Chlorella cells and its stimulative effect on phagocytic activity of rat reticuloendothelial system", Nippon Nogei Kagaku Kaishi 46:373–80 (short description).

White et al., (1972) "Acidic polysaccharide from cell wall of *Chlorella pyreinodosa*", Biochem. Biophys. Acta. 264:117–28 (short description).

Shnyukova E.I. N.G. Kholodnil Inst. Bol., Kiev, USSR., "Reserve polysaccharides of green microalgae", Ukr. Bot. Zh. (1990), 47(1):57–62 (abstract in English).

Kaplan et al., "Chelating properties of extracellular polysaccharides from Chlorella spp.", Appl. Environ. Microbiol. (1987), 53(12):2953–6 (partial abstract in English).

Mizuno et al., "Studies on the carbohydrates of Chlorella. III. Fractionation and some biological activities of the Chlorella polysaccharides", Shizuoka Daigaku Nogakubu Konkyu Hokoku (1980), (30):51–9 (abstract in English).

Shino, K. Chlorella Gijutsu Kaihatsu Proj. Team, Japan. "Cell walls and polysaccharides of chlorella", New Food Ind. (1980), 22(7):18–32 (English title).

Klyushkina et al., "Hydrolysis of cell–wall polysaccharides of the leaf–stem mass of higher plants and chlorella" USSR. Nov. v Poluchenii I Primenenii Fermentov. M. (1978), 94–1000. From: Ref. Zh. Biol. Khlm. 1979, Abstr. No. 19Kh469 (translated title).

* cited by examiner

Stimulation of splenocytes' proliferation *in vitro* after treatment with products of IBP-2 resolution with Sephadex G 100

FRACTIONS OF CHLORELLA EXTRACT CONTAINING POLYSACCHARIDE HAVING IMMUNOMODULATING PROPERTIES

REFERENCE TO RELATED APPLICATIONS

This application claims the benefit of U.S. Provisional Application No. 60/224,014, filed Aug. 10, 2000, the content of which is herein incorporated by reference.

FIELD OF INVENTION

The present invention relates to Chlorella extracts for use as immunomodulators.

BACKGROUND OF THE INVENTION

Chlorella is a unicellular green algae that has been called a sun-powered supernutrient. Attested beneficial properties of this edible microalgae include wound healing, detoxification, constipation relief and growth stimulation. A number of studies have also indicated that Chlorella has beneficial effects on the immune system, both in vitro and in vivo.

Chlorella occurs in both fresh water and marine water. Species of the Chlorella genus exhibit striking diversity of physiological and biochemical properties (Kessler, E. "Phycotalk" 1989, 1:141–153; V. Rastogi Publ., New Delhi, India). Chlorella produces little cellulose and other indigestible cell wall material, and hence has been extensively investigated as a possible new source of food, especially as feedstock (Lee, Robert E. "Phycology" $2^{nd}$ edition; 1989, page 281; Cambridge University Press).

Chlorella has the highest content of chlorophyll of any known plant. It also contains vitamins, minerals, dietary fibre, nucleic acids, amino acids, enzymes, etc. It contains more than 9% fats (out of which polyunsaturated fatty acids [PUFA] represent about 82%). The vitamin content consists of provitamin A, vitamins $B_1$, $B_2$, $B_6$, niacin, $B_{12}$, biotin, vitamin C, vitamin K, pantothenic acid, folic acid, choline, lipoic acid, ionositol, PABA etc. Among the minerals present the most important are P, K, Mg, S, Fe, Ca, Mn, Cu, Zn and Co. The main components of Chlorella cells are about 60% protein (composed of all basic amino acids), and 20% carbohydrate.

Aqueous extracts of *Chlorella pyreinodosa* has been used for its nutritive content as well as for other health benefits. Studies report on numerous health benefits including improved immune system function and detoxification of harmful toxins. It was introduced as a health food in the USA in 1977 when novel technology processes were developed which made it more digestible and has been the largest selling health food supplement in Japan for a number of years. The Taiwan Chlorella company is the world's largest supplier of Chlorella, and sells the product worldwide to Asia, Europe and North America, under the following brand names: Algea, Bio-REURELLA, Green Gem, Green Boost, Green Nature, Green Power, Joyau Vert and Natural Boost.

A number of studies have documented *C. vulgaris* extracts which have anti-tumor activity, as well as activity against Listeria and *E. coli* (Tanaka et al. Immunopharmacol. Immunotoxicol., 1990, 12(2):277–291; Tanaka et al. Cancer Immunol. Immunother., 1998, 45(6):313–320; Hasegawa et al. Int. J. Immunopharmacol., 1990, 12(8):883–891). These activities appear to be immune-mediated rather than direct toxicity against the tumor or pathogen.

A number of Chlorella extracts are available commercially, including products by Swiss Herbal and Nature's Way. The Swiss Herbal product is identified as pure Chlorella broken cells containing Protein 61%, Carbohydrate 21.1%, Fat 11.0%, Chlorophyll 2.866%, RNA 2.94% and DNA 0.28%.

Other publications related to the present field include the following:

Japanese patent application laid open No. Sho 58-15920 discloses polysaccharides from fresh water Chlorella having immune potentiator and anti-tumor activity.

Neveu et al. Experientia, 1978, 34(12):1644–1645 discloses that *C. pyrenoidosa* is an immune response modulator.

Vermeil and Morin CR Seances Soc. Biol. Fil., 1976, 170(3):646–649 discloses that *C. pyrenoidosa*, presumably by nature of its cell wall, protects mice against sarcoma grafting.

Miyazawa et al. J. Ethnopharmacol., 1988, 24(2–3):135–146 discloses that *C. pyrenoidosa* cells or extract mediate host immune enhancement of the anti-tumor response.

Umezawa et al. Chemotherapy, 1982, 30(9):1041–1046 and Komiyama et al. Chemotherapy, 1986, 34:302–307 disclose that the acidic polysaccharide Chlon A from *C. pyrenoidosa* has immune enhancing and anti-tumor effects. Chlon A contains rhamnose, arabinose, glucose, galactose and glucuronic acid.

White and Barber Biochimica Biophysica Acta, 1972, 264:117–128 discloses an 88 kDa acidic polysaccharide from *C. pyrenoidosa* containing mainly rhamnose, as well as arabinose, galactose, xylose, mannose and glucuronic acid.

U.S. Pat. No. 4,533,548 discloses acidic polysaccharide CH-1 from *C. pyrenoidosa* containing mainly rhamnose, as well as arabinose, galactose, glucose and glucuronic acid. The polysaccharide was obtained via gel filtration with Sephadex G-75.

U.S. Pat. No. 4,831,020 discloses a polysaccharide extract from *C. minutissima*, a marine Chlorella, with immune-stimulating and anti-tumor activity. This patent states that polysaccharides from marine Chlorella species are more effective in activating immunity than fresh water Chlorella species. The polysaccharide extract was obtained via gel filtration with Sephadex G-50.

U.S. Pat. No. 4,786,496 discloses a lipid and glycolipid fraction of marine Chlorella with immuno-potentiating activity.

Kojima et al. J. Retic. Soc., 1973, 14:192–208 discloses a 1,250–1400 Da reticuloendothelial system (RES)-active glucan from Chlorella.

U.S. Pat. No. 3,462,412 discloses a process for preparing a RES-stimulating extract from Chlorella.

Japanese patent application, publication no. 06248003 discloses a Chlorella extract of 15 to 25 kDa, comprising polysaccharides containing predominantly galactose, with anti-neoplastic activity.

Mizuno et al. Bull. Fac. Agr. Shizuoka Univ. (Shizuoka Daigaku Nogakubu Kenkyu Hokoku), 1980, 30:51–59 discloses two fractions of neutral glycans from Chlorella, both apparently of small molecular weight.

Ukai et al. Ann. Proc. Gifu Pharm. Univ. (Gifu Yakka Daigaku Kiyo), 1990, 39:44–48 discloses two polysaccharides, CP-I and CP-II, from *C. pyrenoidosa* with RES-stimulating activity. CP-I comprises glucose, fucose, rhammose, galactose and mannose; CP-II comprises glucose, galactose, rhamnose and mannose.

Chu et al. Aquaculture, 1982, 29(3–4):241–252 discloses that the polysaccharide, ethanol-precipitable fraction of five algal species including Chlorella contains principally glucose, mannose, ribose/xylose, rhamnose and fucose.

SUMMARY OF THE INVENTION

Chlorella extracts prepared according to the invention show immune stimulatory activity in pharmacological and clinical tests. In one aspect, the extracts provided by the present invention have a higher immune stimulatory activity than extracts prepared and used in the art.

In one aspect, the invention provides preparations comprising high molecular weight Chlorella polysaccharide and polysaccharide complexes. The high molecular weight polysaccharide and polysaccharide complexes are about $1 \times 10^5$ Da to about $1 \times 10^7$ Da and constitute at least 22% (w/w) of the total Chlorella-derived content of the extract. In a preferred embodiment, the extract is derived from *Chlorella pyrenoidosa*.

The high molecular weight polysaccharide and polysaccharide complexes may be of a selected range, e.g. about $1 \times 10^5$ Da to about $3 \times 10^5$ Da, about $3 \times 10^5$ Da to about $5 \times 10^5$ Da, about $5 \times 10^5$ Da to about $6 \times 10^5$ Da, about $6 \times 10^5$ Da to about $7 \times 10^5$ Da, about $7 \times 10^5$ Da to about $8 \times 10^5$ Da, about $8 \times 10^5$ Da to about $9 \times 10^5$ Da, about $9 \times 10^5$ Da to about $1 \times 10^6$ Da, about $1 \times 10^6$ Da to about $2 \times 10^6$ Da, about $2 \times 10^6$ Da to about $3 \times 10^6$ Da, about $3 \times 10^6$ Da to about $4 \times 10^6$ Da, about $4 \times 10^6$ Da to about $5 \times 10^6$ Da, about $5 \times 10^6$ Da to about $7 \times 10^6$ Da, about $7 \times 10^6$ Da to about $9 \times 10^6$ Da, and about $9 \times 10^6$ Da to about $1 \times 10^7$ Da.

The extracts may contain various different percentages of polysaccharide and polysaccharide complexes as a fraction of the total Chlorella-derived content of the extract. The percentage may be at least 24% (w/w), at least 26% (w/w), at least 28% (w/w), at least 30% (w/w), at least 35% (w/w), at least 40% (w/w), at least 45% (w/w), at least 50% (w/w), or at least 60% (w/w).

In another aspect, the high molecular weight polysaccharide and polysaccharide complexes contain glucose and any combination of: galactose, rhamnose, mannose and arabinose.

In another aspect, the high molecular weight polysaccharide and polysaccharide complexes is substantially free of ribose, nucleic acids, ribonucleic acids and unassociated proteins. The high molecular weight polysaccharide and polysaccharide complexes may also contain N-acetyl glucosamine and N-acetyl galactosamine.

In another aspect, the extracts of the invention retain immunomodulating activity upon treatment to remove unassociated DNA, RNA and proteins. Such treatment includes digestion by pronase, DNAse, RNAse and proteases.

In another aspect, the extracts of the invention retain immunomodulating activity upon treatment to effect cleavage of specific glycosidic linkages, the linkages being defined by their susceptibility to cleavage by amylase, amyloglucosidase, cellulase or neuraminidase. Such susceptible linkages are typically:

(i) three or more α-1,4-linked D-glucose units;

(ii) α-1,4-linked glucosides;

(iii) α-1,4-linked galactosides; or (iv) α-1,4-linked D-glucose.

The invention also provides nutritional compositions containing the high molecular weight Chlorella extract with at least one energy source which may be carbohydrates, fats or nitrogen.

The extracts of the invention may also be used in combination or in mixture with a conventional supplement such as vitamin E, vitamin C and folic acid. The extracts may also be used with other nutraceuticals such as fish oils, spirulina and echinacea, especially those nutraceuticals which have immunostimulant activity.

The invention also provides a process for obtaining Chlorella preparations having immunomodulating activity. The process contains the steps of:

(a) size fractionating an aqueous extract of Chlorella, and (b) selecting fractions comprising high molecular weight polysaccharide and polysaccharide complexes of about $1 \times 10^5$ Da to about $1 \times 10^7$ Da.

The process for obtaining the Chlorella extract may further include the step of pooling and concentrating the selected fractions. Size fractionation may be achieved by chromatography, ultrafiltration or ultracentrifugation.

The invention also provides a method for modulating the immune response of a mammal including humans by administering to the mammal an effective amount of the high molecular weight Chlorella extract. Such modulation includes increased proliferation of splenocytes and increased production of cytokines such as IL-6, IL-10, INF-γ and TNF-α, and may be advantageously used to treat or prevent bacterial or fungal infections.

The extract may further be administered as a supplement to a vaccination regimen to further stimulate the immune response. A flu vaccine may be advantageously used with the extract. The extract may be present as an adjuvant to the vaccines, especially as an oral vaccine adjuvant.

BRIEF DESCRIPTION OF THE DRAWINGS

The invention in its various embodiments will now be described with reference to the attached drawings.

DETAILED DESCRIPTION OF THE INVENTION

Figure 1:
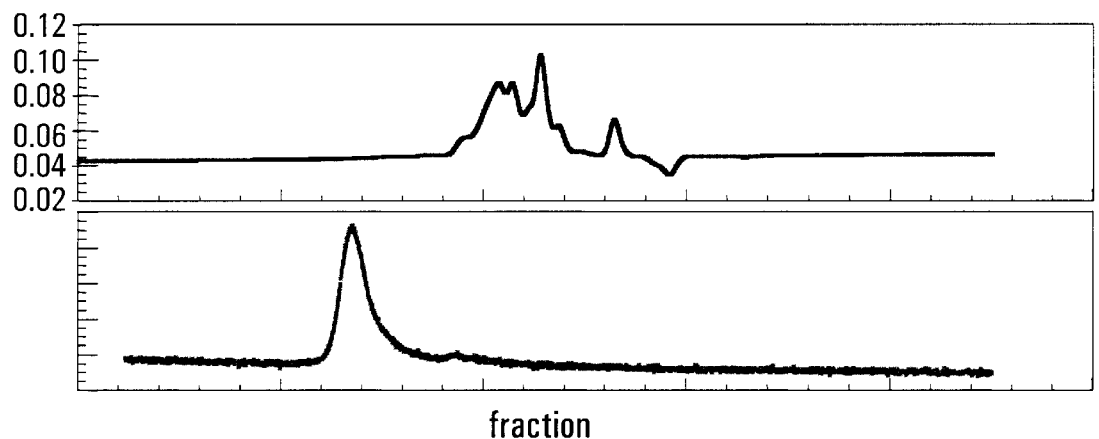
FIG. 1: Combination size-exclusion chromatography (SEC)/refractive index detection (RI)/multi-angle laser light scattering (MALS) chromatogram of immune booster preparations IBP-1 or IBP-2. The top trace is the RI chromatogram; the bottom trace is the MALS response.

The present invention relates to a method for enhancing immunity defence mechanisms of mammals including humans. Immunity defences are enhanced by the administration of Chlorella-derived immunomodulators in the form of Chlorella-derived extracts of molecular weights between $1 \times 10^5$ Da and $1 \times 10^7$ Da.

A. Chlorella

Species of the Chlorella genus used in the invention includes the following: minutissima, marina, salina, pyrenoidosa, vulgaris, anitrata, antarctica, autotrophica, regularis, among others (see World Catalog of Algae, $2^{nd}$ Edition, pages 58–74; Miyachi et al. (Eds); 1989; Japan Scientific Societies Press, the content of which is herein incorporated by reference).

Mutant strains of Chlorella, either naturally occurring or artificially produced, for example by irradiation (e.g. ultraviolet, X-ray), chemical mutagens or by site-directed mutagenesis, are within the scope of the invention. In one embodiment, *C. pyrenoidosa* and its variants are preferred. In another embodiment, *C. ellipsoidea* and its variants are preferred. Cultivation of Chlorella is carried out by methods known in the art using suitable media and culture conditions (see for example, White and Barber, Biochimica Biophysica Acta., 1972, 264:117–128). Polysaccharide production may be influenced by physiological and metabolic manipulation. Composition of the growth media may influence growth rate leading to changes in cell wall thickness. Genes responsible for growth may be up- or down-regulated. For a method used to transform eukaryotic algae, see for example U.S. Pat. No. 6,027,900; for methods to select algal mutants, see for example U.S. Pat. No. 5,871,952. Thus, by selection under various conditions, variants of biopolymer immunomodulators from Chlorella may be manufactured.

B. Chlorella Extracts and Their Preparation (a) Preparation of Crude Extract

Crude aqueous extracts of Chlorella are prepared by methods known in the art, including hot water extraction of cultured cells or spray dried cells (U.S. Pat. Nos. 4,831,020 and 5,780,096) and solvent extraction methods (White and Barber, Biophys. Biochim. Acta, 1972, 264:117–128; U.S. Pat. No. 3,462,412). Crude extracts may be obtained from the Taiwan Chlorella company (www.taiwanchlorella.com/product-3.htm).

In one embodiment, the crude extract is prepared from spray-dried Chlorella cells with an average moisture content of 0.3%; (the moisture content was determined after drying the spray-dried material for 16 h under a vacuum of 5 mm). The crude extract is prepared by treating the cells with aqueous media, preferably water or weak solutions of organic acids, such as acetic acid, ascorbic acid, benzoic acid, citric acid, lactic acid, maleic acid, propionioc acid, sorbic acid, succinic acid etc., preferably benzoic acid, under gentle agitation. The extraction process could be executed at various temperatures ranging from 0 to 100° C., preferably between 50 and 90° C. The yields and immunoactivity correlating with chromatographic profiles indicate that 1 h at 80° C. is a suitable combination of time and temperature to perform this step efficiently.

The residual cells and the cell debris were separated by centrifugation with a relative centrifugal force (RCF) of 150 to 10,000 g, preferably 4,000 to 10,000 g. The time necessary to complete this step is in relation to the centrifugal force; 20 min. is sufficient at 10,000 g. The supernatant was then micro-filtered. Alternatively, filtration may be used to remove whole cells and debris, in which case use of a series of filters starting from coarse, through medium and ending with micro-filtration, is necessary. Cross-flow filtration or vibrating membrane technology is recommended to reduce fouling. Filtration is particularly sensitive to temperature and time period required for extraction. Centrifugation is therefore the preferred route.

After centrifugation or filtration, the supernatant (or filtrate) may be dried to obtain IBP-1 products in dry form. The drying was achieved by lyophilization, cold airflow, or preferably by spray-drying. Alternatively, the volume of the extract could be reduced first (to 10–50%, preferably 20%), and then the active materials precipitated from the solution with suitable precipitants, preferably ethanol or ammonium sulfate.

IBP-1 was liberated from salts and low molecular mass products. Although a variety of aqueous media (such as diluted alcohols, various buffers, diluted acetic acid, etc.) could be employed, water was found to be a sufficient medium for the dialysis. This step reduced the mass of the extracted material by about 50% and increased its specific immunoactivity (as judged by effect on stimulation of splenocytes, see below) by about 25%. Dialysis could be replaced by desalting with gel filtration media, such as Sephadex G 25, Bio Gel P 6 or equivalents. Similarly, corresponding ultrafiltration membranes with corresponding molecular weight cut-offs could be used. After the desalting step, the material (IBP-2) may be dried using methods described for IBP-1.

(b) Size Fractionation of Extracts

Size fractionation of Chlorella extracts can be accomplished by any method known in the art, including size exclusion chromatography, sedimentation analysis e.g. gradient centrifugation, and ultra-filtration.

IBP-1 or IBP-2 is a mixture of polysaccharides and polysaccharide complexes, with average molecular mass of the immunomodulatory fraction of interest ranging from 100 up to 10,000 KDa. Polysaccharide complexes are polysaccharides which are non-covalently associated with a non-polysaccharide biopolymer which, by itself, has no significant immune activity. Non-polysaccharide biopolymers include DNA and protein which may contribute to the cumulative molecular weight of the extract but which has no significant immune activity.

In various embodiments, the high molecular weight polysaccharide and polysaccharide complexes are about $1 \times 10^5$ Da to about $1 \times 10^5$ Da, about $3 \times 10^5$ Da to about $5 \times 10^5$ Da, about $5 \times 10^5$ Da to about $6 \times 10^5$ Da, about $6 \times 10^5$ Da to about $7 \times 10^5$ Da, about $7 \times 10^5$ Da to about $8 \times 10^5$ Da, about $8 \times 10^5$ Da to about $9 \times 10^5$ Da, about $9 \times 10^5$ Da to about $1 \times 10^6$ Da, about $1 \times 10^6$ Da to about $2 \times 10^6$ Da, about $2 \times 10^6$ Da to about $3 \times 10^6$ Da, about $3 \times 10^6$ Da to about $4 \times 10^6$ Da, about $4 \times 10^6$ Da to about $5 \times 10^6$ Da, about $5 \times 10^6$ Da to about $7 \times 10^6$ Da, about $7 \times 10^6$ Da to about $9 \times 10^6$ Da, and about $9 \times 10^6$ Da to about $1 \times 10^7$ Da.

Size fractionation to obtain the above fractions is based on principles of molecular sieving. Typically, size exclusion chromatography techniques and ultrafiltration methods are employed. The basic principles of size exclusion chromatography are well known to those in the art, and are explained in "Gel filtration: Principles and Methods. Eighth edition, Amersham Pharmacia Biotech AB, Rahhms I Lund, Uppsala, Sweden". The appropriate columns for fractionating particular ranges can be readily selected and effectively used to resolve the above fractions, e.g. Sephacryl S 100 HR, Sephacryl S 200 HR, Sephacryl S 300 HR, Sephacryl S 400 HR and Sephacryl S 500 HR or their equivalents. In an analogous fashion, Sepharose media or their equivalents, e.g. Sepharose 6B, 4B, 2B, could be used.

Figure 16:
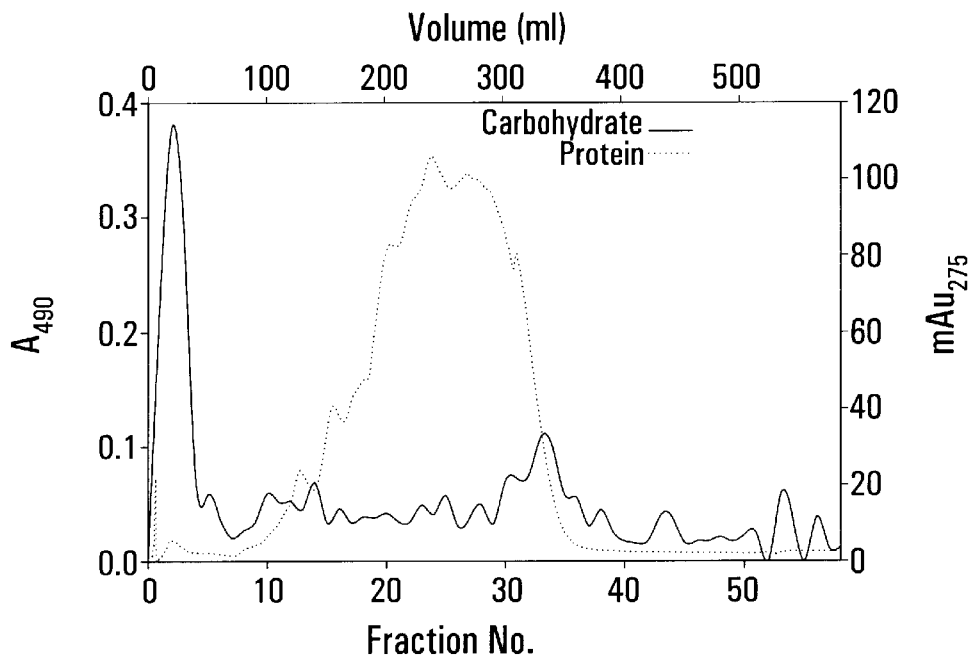
FIG. 16: DEAE Sepharose Fast Flow of IBP-2. A sample was applied on Pharmacia 1.0×30 cm column and eluted with piperazine/HCl (0.02 M, pH 8.8) buffer at a rate of 5 mL/min. NaCl gradient was employed: 0–20% in 20 column volumes, then 20–100% in 2 column volumes.
Figure 17:
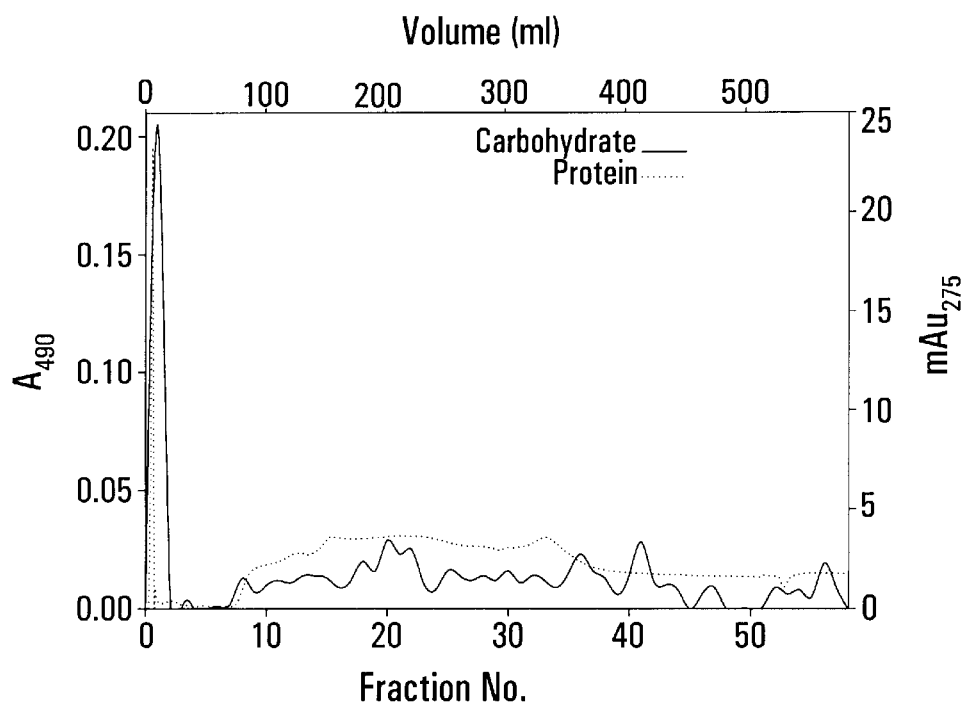
FIG. 17: DEAE Sepharose Fast Flow of retention portion after IBP-2 was passed through an ultrafiltration membrane with MWCO 1 MDa. A sample was applied on Pharmacia 1.0×30 cm column and eluted with piperazine/HCl (0.02 M, pH 8.8) buffer at a rate of 5 mL/min. NaCl gradient was employed: 0–20% in 20 column volumes, then 20–100% in 2 column volumes.

Purification of the polysaccharides or polysaccharide complexes with protein could be achieved in combination with other chromatography techniques, including affinity chromatography, ion exchange, hydrophobic interaction chromatography etc. An example of IBP-2 (the retainate after IBP-2 was passed through ultrafiltration membrane with MWCO>1 MDa) chromatography using DEAE-Sepharose Fast Flow anion exchange chromatography is given in FIGS. 16 and 17. The figures demonstrate significant decrease in the protein content after IBP-2 was passed through the ultrafiltration membrane.

Ultrafiltration of the samples could be performed using molecular membranes with appropriate molecular mass cut-offs. The specific membranes and procedures used to effect fractionation are widely available to those skilled in the art, as outlined in http://www.uku.fi./laitokset/anat/PG/c_method.htm.

In one embodiment, the method used for characterising and quantifying these materials is based on combined size exclusion chromatography (SEC)/multi-angle laser light scattering (MALS)/refractive index detection (RI). In the hybrid technique (SEC/MALS/RI), an isocratic HPLC experiment using a Tosohaas GMPWXL SEC column is used to separate mixtures according to molecular size. On-line MALS determines the average molecular weight distribution of the eluting biopolymers and hence provides specificity in the analysis. RI detection is used both for quantification and to provide the elution profile required in processing the MALS data.

Figure 2:
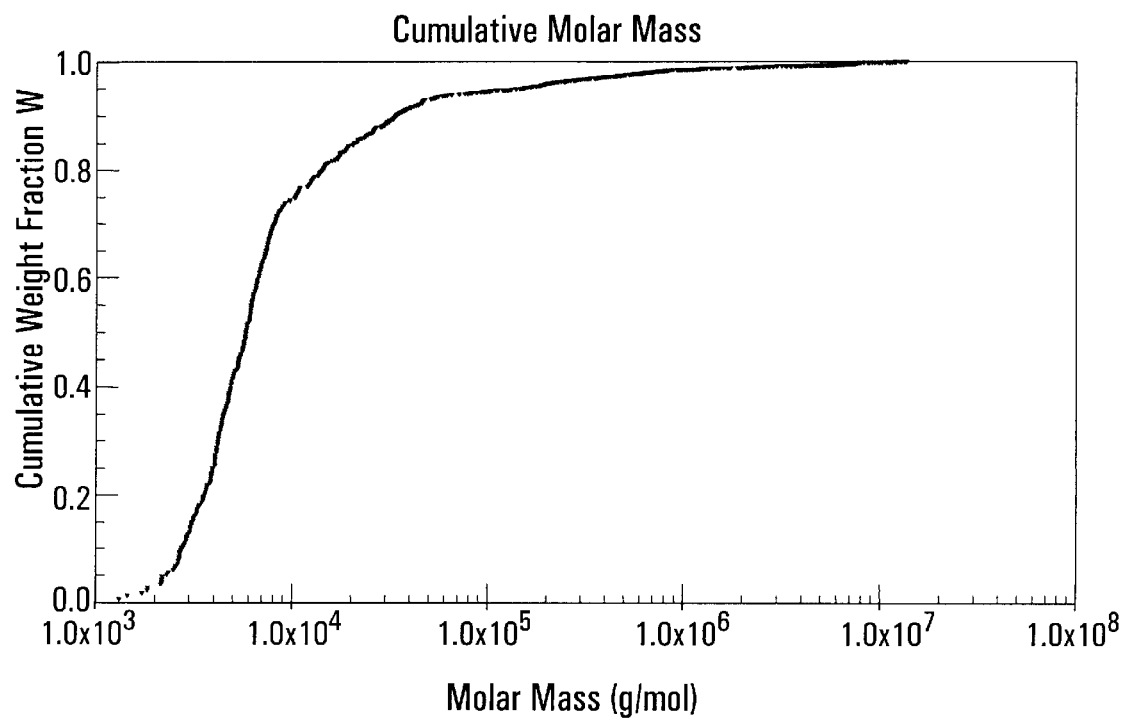
FIG. 2: Cumulative molecular weight profile of IBP-1.

An example of the SEC chromatogram obtained for a typical extract is shown in FIG. 1. The top trace is the chromatogram recorded using the RI detector while the bottom trace is the MALS response at one of the detectors (90 degrees). The MALS peak is a maximum for the high molecular mass component which actually corresponds to a small percentage of the total extract as can be seen from the upper trace. Thus, although the molecular weight range extends from a few KDa to about 10 MDa, the weight average molecular weight (MW) for the entire extract is determined to be around 90 kDa. This can be seen most clearly from the cumulative molecular weight profile of IBP-1 (FIG. 2).

IBP-1 or IBP-2 can be further fractionated using suitable chromatographic or ultrafiltration techniques. Size exclusion chromatography matrices with wide fractionation range such as Sephacryl S 1000 SF (FIG. 3) resolved the extract into two peaks: the first eluted just after the void volume; its average molecular mass, as measured by MALS, averaged 1,000 KDa; the second peak eluted just after the first peak. The combined fractions representing the first peak were desalted and dried analogously to that of IBP-1, resulting in IBP-3. This material was superior in its immunoactivity compared to the second peak (IBP-4). Aqueous media were used in this chromatography procedure, preferably 0.15 M NaCl. Although IBP-1 exhibited higher immunoactivity than the IBP-2, the difference was insignificant. The contribution to the immunostimulant activity (increasing gradually with mass) starts levelling off when molecular mass reaches around 500 KDa.

Figure 4:
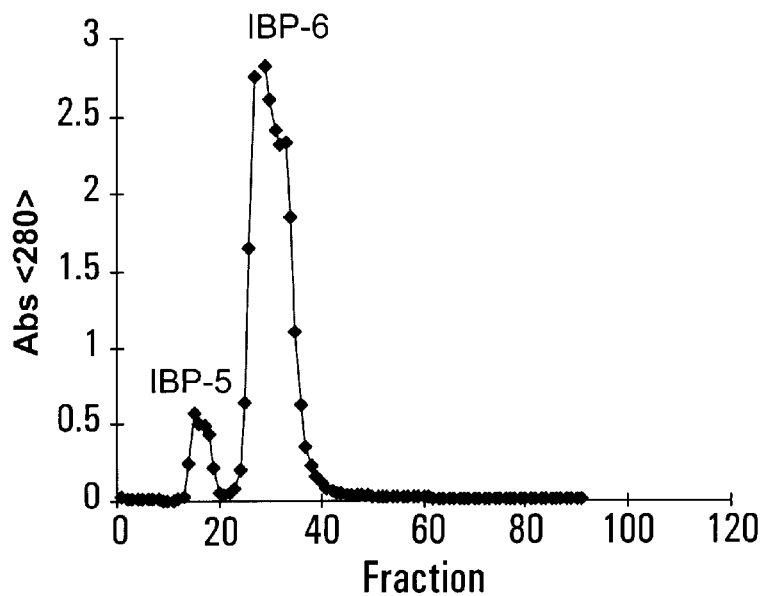
FIG. 4: SEC chromatogram of IBP-2 (or IBP-1) using Sephacryl S 300 HR.
Figure 5:
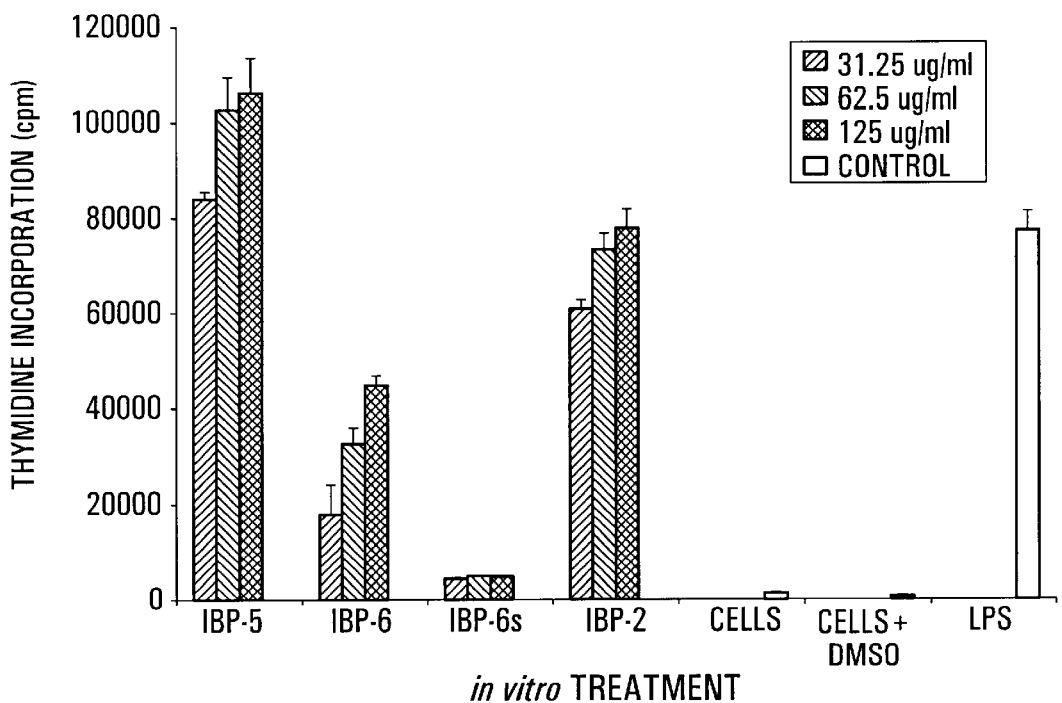
FIG. 5: Stimulation of splenocyte proliferation by various Chlorella extract fractions resolved by Sephacryl S 300 HR; IBP-6s is the peak shoulder fraction of IBP-6; 'Cells' and 'Cells+DMSO' are negative controls; LPS is lipopolysaccharide, used as a positive control.

IBP-4 could be further fractionated using suitable chromatographic or ultrafiltration techniques. Both ion exchange chromatography (IEC) and SEC were found to be useful for further resolution of IBP-4. SEC matrices with the appropriate fractionation range, for example Sephacryl S 300, could be used. Sephacryl S 300 HR resolved IBP-1 or IBP-2 into two peaks (FIG. 4). The first peak started eluting in the very last fractions of the void volume of the column. The majority of the eluted biopolymers exhibited molecular masses ranging from 100 to 500 KDa. The combined fractions representing the first peak were desalted and dried analogously to that of IBP-1, resulting in IBP-5. This material was superior in its immunoactivity to the second peak (IBP-6) which eluted just after the first peak touched the baseline (FIG. 5). IBP-5 represented typically only 30% of the combined mass of both peaks. Aqueous media were used for this chromatography procedure, preferably a 0.1M acetate, pH 4.5 buffer with linear NaCl gradient. The difference in the immunoactivity of IBP-5 and IBP-6 was higher than in that between IBP-3 and IBP-4; typically the ratio of $CPM_{IBP-3}$ to $CPM_{IBP-4}$ was 5:2, as measured by the level of $^3$H-incorporation into proliferating splenocytes. The process could be, to some extent, simplified by use of ultrafiltration membranes with molecular mass cut-off of about 500 KDa. For instance, Omega ZM 500 membrane successfully could be used.

Figure 6:
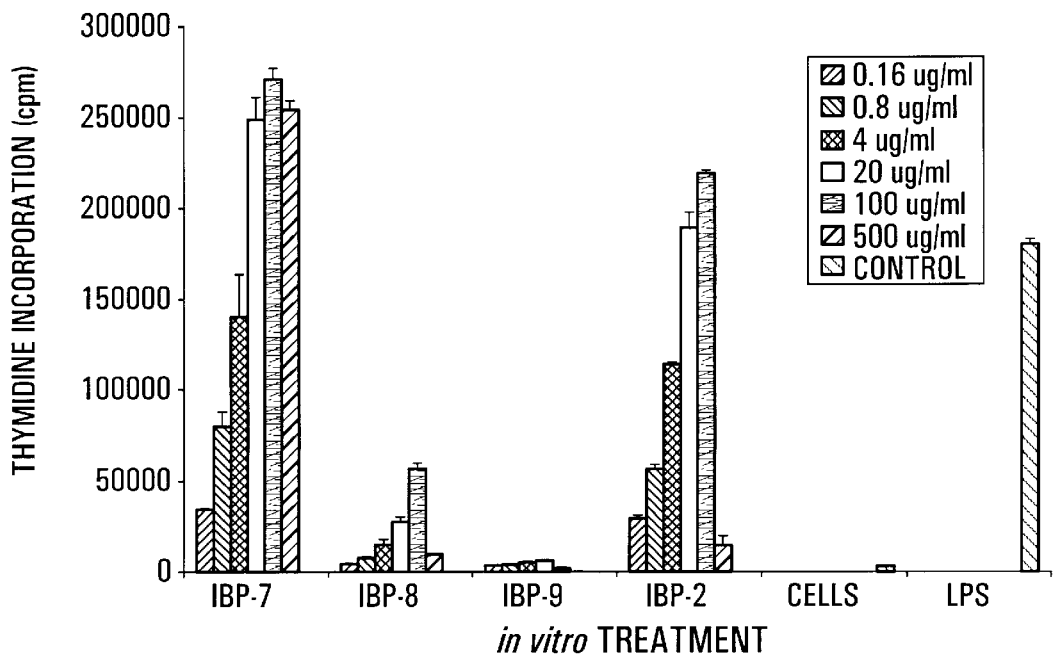
FIG. 6: Stimulation of splenocyte proliferation by various Chlorella extract fractions resolved by Sephadex G100 chromatography of IBP-2; 'Cells' is a negative control; LPS is a positive control.

IBP-6 could be further fractionated using suitable chromatographic or ultrafiltration techniques, for instance using chromatographic matrices such as Sephadex G 100, Sephadex G 75 or analogous media or corresponding ultrafiltration membranes. However, specific immunoactivity residing in IBP-6 was significantly weaker than that of IBP-3 and IBP-5, and therefore was not of prime interest. However, Sephadex G 100 could be efficiently used to remove from IBP-2 the majority of lower molecular weight material (IBP-8), which is associated with low immunoactivity (FIG. 6). Typically the ratio of $CPM_{IBP-7}$ to $CPM_{IBP-8}$ was 10:1; (IBP-7 being the high molecular mass and immunoactive fraction). This purification step could be achieved just as well with a YM-100 ultrafiltration membrane.

Crude extracts of Chlorella contain about 61% protein and 21% carbohydrate. Processing of Chlorella according to the present invention results in a higher percentage of polysaccharide and polysaccharide complexes, i.e. the extracts of the invention have a higher percentage of polysaccharide and polysaccharide complexes relative to the total material derived from Chlorella, compared to a crude extract from broken cells. It is understood that materials unrelated to Chlorella may be added to the Chlorella extract and that such extracts are within the scope of the invention.

The percentage of polysaccharide and polysaccharide complexes in the extracts of the invention is at least 23% (w/w) of the total Chlorella-derived content of the extract. In various embodiments, the percentage is at least 24% (w/w), at least 26% (w/w), at least 28% (w/w), at least 30% (w/w), at least 35% (w/w), at least 40% (w/w), at least 45% (w/w), at least 50% (w/w), or at least 60% (w/w).

The high molecular weight polysaccharide and polysaccharide complexes may be further purified and isolated to the various percentages indicated above by removal of non-polysaccharide components. Such non-polysaccharide components include DNA, RNA and unassociated proteins. (Unassociated proteins are defined for the purpose of the present application as proteins which are not associated with polysaccharides in a polysaccharide complex).

One method of removal is the use of digestion enzymes to cleave the non-polysaccharide components, followed by size fractionation to remove the cleaved products as described in the Examples below (Example 7). Digestion enzymes include pronase, ribonuclease, DNase and proteases, as well known in the art and described in various text books, one example of which is Maniatis et al., Molecular Cloning: A Laboratory Manual (1982) Cold Spring Harbor Laboratory Press, Cold Spring Harbor, N.Y. Proteases useful for digestion of unassociated proteins include: endo- and exopeptidases, pronase, serine proteases such as trypsin, chymotrypsin and subtilisin, thiol proteases such as papain, and calcium-requiring proteases such as thermolysin.

Alternatively, non-polysaccharide components may be removed by affinity chromatography, for example by use of DNA- or RNA-binding matrices (Maniatis et al., 1982). Another option is to purify the polysaccharide and polysaccharide complexes away from the contaminating components by use of polysaccharide binding matrices such as lectins. In another embodiment, the extracts of the invention may be treated with glycosidic enzymes under conditions and for a length of time sufficient to effect cleavage of:

(i) three or more α-1,4-linked D-glucose units;
(ii) α-1,4-linked glucosides;
(iii) α-1,4-linked galactosides; or
(iv) α-1,4-linked D-glucose.

Examples of glycosidic enzymes useful for cleavage of such glycosidic linkages include: amylase, amyloglucosidase, cellulase and neuraminidase.

C. Characterization of Extracts

Carbohydrate composition, DNA content and amino acid composition of the Chlorella extracts of the invention can be determined by any suitable method known in the art.

Immune activity of the extracts of the invention are associated with high molecular weight Chlorella polysaccharides, defined as those macromolecules consisting of monosaccharides joined by glycosidic linkages. The polysaccharides are present in the extracts in the form of free polysaccharides or complexed polysaccharides (i.e. polysaccharides which are non-covalently associated with a non-polysaccharide biopolymer which, by itself, has no significant immune activity). In one embodiment, the protein content of the extract is about 20% to 50%, preferably 20% to 30%. Of this percentage of proteins, about 40% to 60% are associated with polysaccharides.

Non-polysaccharide biopolymers include DNA, protein and possibly RNA, which may contribute to the cumulative molecular weight of the extract but which has no significant immune activity. Unassociated RNA, DNA and protein, i.e. those not complexed with the polysaccharides, do not contribute significantly to immune activity of the extracts. For the purposes of the present application, unassociated RNA, DNA and protein are defined functionally as those RNA, DNA and protein which are susceptible to cleavage by ribonuclease (RNAse), deoxyribonuclease (DNAse) and common proteases of the serine and thiol class. The extracts of the present invention may thus be essentially free or substantially free of unassociated RNA, DNA and protein. By "essentially free" is meant less than 5% unassociated DNA or RNA and less than 15% unassociated proteins. By "substantially free" is meant less than 2% associated DNA or RNA and less than 10% unassociated proteins.

It is understood that, while the non-polysaccharide biopolymers per se lack immune activity, their association with the polysaccharides may contribute to the immune activity of the polysaccharides since the non-polysaccharide biopolymers of the complex may fulfill certain steric or polar requirements which enable the polysaccharides to function effectively as immunomodulators.

The extracts of the present invention may be digested with amylase, amyloglucosidase, cellulase and neuraminidase without significant loss of immune activity. Immune activity thus apparently resides in polysaccharides or their complexes which do not contain a substantial amount of three or more α-1,4-linked D-glucose units; α-1,4-linked glucosides; α-1,4-linked galactosides; or α-1,4-linked D-glucose. However, it is understood that immunomodulatory polysaccharides may contain the above glycosidic linkages if such linkages are not accessible to enzyme digestion.

D. Uses of Extracts

Biological response modifiers have been defined as those agents that modify the host's biological response by a stimulation of the immune system, which may result in various therapeutic effects. One of the categories of substances belonging to this class is immunomodulators. As used herein, the term "immunomodulator" refers to an agent which is able to modulate an immune response. In the context of the present invention, such modulation is an enhancement of the host's immunity defence mechanism.

Chlorella extracts are thought to be primarily a B-cell and macrophage stimulator. One benefit of B-cell immunomodulators is that they can stimulate immune function in those who may have an impaired antibody response to an antigen. Also, a B-cell stimulator might increase the rapidity of the antibody immune response when presented with a new infection. Chlorella extracts provide a safe, efficacious and cost effective alternative for preventative health treatment.

In vitro studies demonstrated that Chlorella extracts stimulated proliferation of BALB/c mouse spleen cells, and macrophage production of IL-6 and $NO_2$. Chlorella extracts were also examined in vivo, and found to significantly reduce infection with *Listeria monocytogenes*, as well as the fungus *Candida albicans* (see Examples 8 to 13).

A series of three toxicology trials have been completed for Chlorella extracts. No effect of Chlorella extract administration was evident during the 28-day oral toxicity study in rats. For the acute oral toxicity in rats, to determine the highest non-lethal or the lowest lethal dose of the product following a single oral administration, the study found that the lowest lethal dose of a crude Chlorella extract was in excess of 2000 mg/kg body weight. The bacterial mutation assay showed that Chlorella extracts did not exhibit any mutagenic activity under the test conditions.

A recently completed randomized, double-blind placebo-controlled study found that Chlorella extracts demonstrated significant immunostimulatory effects in healthy adults receiving the influenza vaccine, compared to placebo subjects (see Example 14).

In vitro experiments with human blood cells show stimulation of production of interleukins, similar to that seen in the mouse model.

Chlorella extracts of the invention are suitable for use in any condition or disease state where immune response enhancement or modulation is desired. In one embodiment, Chlorella extracts may be used in an effective amount as adjuvants in various forms of mucosal vaccine preparations, especially for oral administration.

Adjuvants may protect the antigen from rapid dispersal by sequestering it in a local deposit, or they may contain substances that stimulate the host to secrete factors that are chemotactic for macrophages and other components of the immune system. Known adjuvants for mucosal administration include bacterial toxins, e.g., the cholera toxin (CT), the *E. coli* heat-labile toxin (LT), the *Clostridium difficile* toxin A and the pertussis toxin (PT). Chlorella extracts, being an edible product of high molecular weight and themselves immune stimulants, are candidates for use as adjuvants in oral vaccines.

The term "effective amount" of an immunomodulator refers to an amount of an immunomodulator sufficient to enhance a host defence mechanism. This amount may vary to some degree depending on the mode of administration, but will be in the same general range. If more than one immunomodulator is used (for example, Chlorella extract in combination with echinacea), each one may be present in these amounts or the total amount may fall within this range. The exact effective amount necessary could vary from subject to subject, depending on the species, age and general condition of the subject, the severity of the condition being treated, the mode of administration, etc. Thus, it is not possible to specify an exact effective amount. However, the appropriate effective amount may be determined by one of ordinary skill in the art using only routine experimentation or prior knowledge in the immunomodulator art.

The term "treatment" as used herein covers any treatment of a mammal, particularly a human, and includes:

(i) preventing the disease from occurring in a subject which may be predisposed to the disease but has not yet been diagnosed as having it;

(ii) inhibiting the disease, i.e., arresting its development; or (iii) relieving the disease, i.e., causing regression of the disease.

E. Form of Extracts

The nutritional and pharmaceutical compositions containing Chlorella extracts of the invention may be formulated and administered in any form suitable for enteral administration, for example oral administration or tube feeding. The formulations are conveniently administered in the form of an aqueous liquid. The formulations suitable for enteral application are accordingly preferably in aqueous form or in powder or granulate form, including tablet form. The powder or granulate may be conveniently added to water prior to use. In liquid form, the compositions have a solid content of typically from 0.1% to 50% by weight, preferably from 1% to 10% by weight. As a drink, the compositions may be obtained by any manner known, e.g. by admixing the Chlorella extract with an energy source such as carbohydrates, fats and nitrogen sources.

The nutritional compositions may be in the form of a complete formula diet (in liquid or powder form), such that when used as sole nutrition source, essentially all daily caloric, nitrogen, fatty acids, vitamin, mineral and trace element requirements are met. However, the nutritional compositions of the invention are preferably intended for use as a dietary supplement.

Pharmaceutical compositions of the invention may also be formulated in a single-dose format, where they comprise Chlorella extracts and a pharmaceutically acceptable carrier. Such pharmaceutical compositions are suitable for enteral administration, such as oral, nasal or rectal administration. Suitable compositions may be in liquid form or solid form. Dosage of liquid compositions are typically from 0.1% to 50% by weight, preferably from 1% to 10% by weight of Chlorella extract. Dosage of solid compositions are typically from 0.2 mg/kg to 200 mg/kg, preferably from 1 mg/kg to 10 mg/kg of Chlorella extract The compositions may be in the form of tablets, hard and soft capsules, and sachets.

Suitable carriers are known in the art. They comprise fillers such as sugars or cellulose, binders such as starch, and disintegrators if required.

The following examples are offered by way of illustration and not by way of limitation.

EXAMPLE 1

Preparation of IBP-1

Twenty grams of dried powder of *Chlorella pyreinodosa* were mixed with 100 mL distilled water and heated under gentle stirring for 1 h at 80° C. The material was centrifuged at 10,000 g for 20 min; the residual pellet was washed twice. The combined supernatants were then micro-filtered and spray dried. The average yield was 10.5%. The extraction of the pellet for 1 h at 80° C. could be repeated several times, preferably twice, instead of simple wash.

Alternatively, the combined supernatants were evaporated to ⅕ of their original volume using a rotary evaporator under reduced pressure, then precipitated with ethanol (80% final ethanol content). The mixture was kept at 4° C. for 18 h, then the precipitate was filtered off, washed with absolute ethanol and vacuum-dried.

EXAMPLE 2

Preparation of IBP-2

The extracted material, prepared as above, was desalted by exhaustive dialysis against water at 4° C. and then spray-dried. The average yield was about 7.5%.

EXAMPLE 3

Chromatography of IBP-2 and Preparation of IBP-3

Figure 3:
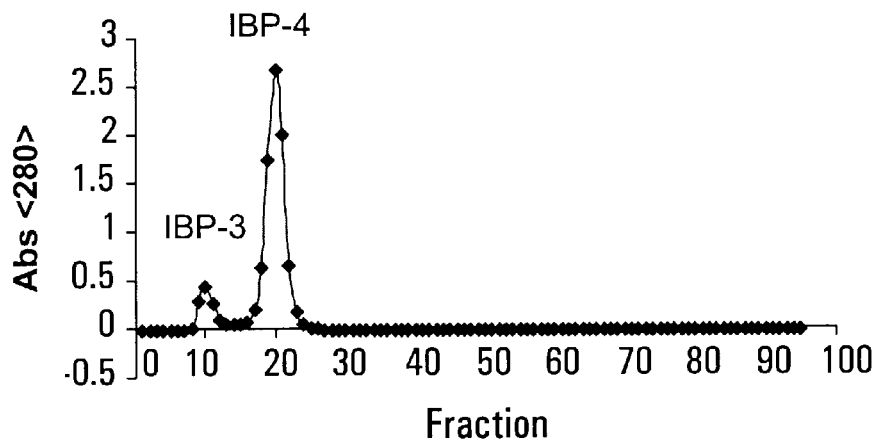
FIG. 3: SEC chromatogram of IBP-2 using Sephacryl S 1000 SF.

Twenty milligrams of IBP-2 were dissolved in 1 mL of distilled water, pre-filtered with a 0.45 $\mu$m filter and loaded on Sephacryl S 1000 HR column (1.0×50 cm) and eluted with 0.15 M NaCl. Chromatography was monitored at 280 nm and at 490 nm after interaction of the eluted fractions with a phenol/sulfuric acid reagent. The mixture was resolved into two peaks. The major immunoactivity was in the high molecular mass peak (IBP-3). However, the lower molecular mass peak (IBP-4) also contained a significant portion of immunoactivity. The chromatogram is shown in FIG. 3.

EXAMPLE 4

Chromatography of IBP-2 and Preparation of IBP-5

Two hundred mg of IBP-2 were dissolved in 10 mL distilled water, pre-filtered with 0.45 μm filter, loaded on a Sephacryl S 300 HR column (2.5×90 cm), and eluted with 0.1 M acetate buffer, pH 4.5 and linear NaCl gradient. Chromatography was monitored at 280 nm, and at 490 nm after interaction of the eluted fractions with a phenol/sulfuric acid reagent. The mixture was resolved into two peaks. The major immunoactivity was in the high molecular mass peak (IBP-5). The lower molecular mass peak (IBP-6) consisted of two fused peaks (an apparent peak shoulder, the fractions of which were tested as IBP-6s, FIG. 5). The SEC profile is shown in FIG. 4.

EXAMPLE 5

Chromatography of IBP-2 and Preparation of IBP-7

Two hundred mg of IBP-2 were dissolved in 10 mL distilled water, pre-filtered with 0.45 μm filter, loaded on Sephadex G 100 column (2.5×90 cm), and eluted with 0.1 M acetate buffer, pH 4.5 and linear NaCl gradient. Chromatography was monitored at 280 nm, and at 490 nm after interaction of the eluted fractions with a phenol/sulfuric acid reagent. The mixture was resolved into two peaks. The major immunoactivity was in the high molecular mass peak (IBP-7). The lower molecular mass peak (IBP-8) retained much less of the activity. IBP-9 represents the fractions following IBP-8 (FIG. 6).

EXAMPLE 6

Compositional Analysis

Dialysis or ultrafiltration demonstrated that only a small portion of immunoactivity was associated with low molecular mass (less than 100 KDa) compounds. The active material is thermally stable and could be precipitated from solution with ethanol or ammonium sulfate. The thermal stability of the extract makes it suitable for spray-drying; indeed, immunomodulatory activity was retained after the spray-drying process. A typical protein content of a fraction is about 30%. DNA content varies from 0% to 20%, with 0% to 2% at molecular masses greater than 100 KDa.

(a) Carbohydrate Composition by Planar Chromatography and Gas Chromatograph (GC)

In one embodiment, the lyophilized extract (or further purified fractions) was dissolved in water (1 mg/mL, 400 μL) and hydrolysed with 1M trifluoacetic acid (TFA, 1 mL) at 100° C., overnight with stirring, in tightly sealed 4 mL screw cap vials. The sample was then evaporated repeatedly to dryness using methanol. The dried hydrolysate was reduced using 0.5 M $NaBH_4$ in 1 M $NH_4OH$ (0.6 mL) under overnight stirring at room temperature. The borohydride was then quenched with acidic methanol (20% acetic acid in methanol, 1 mL) and the mixture evaporated to dryness.

Three mL of acetic anhydride were added to the sample; the mixture was heated in a water bath to 80° C. for 2 h to produce acetyl alditols and then evaporated to dryness.

The acetyl alditol samples were extracted by distributing the reaction mixture between ethyl acetate and water; the organic phase was used directly for gas chromatography/mass spectroscopy (GC-MS) analysis.

All standards and sample extracts were dissolved in ethyl acetate and concentrated to approximately 100 μL. Samples were injected using the split mode of a Thermoquest Trace 2000 gas chromatograph at a 10:1 split and chromatographed on an SGE BPX70 capillary column (30 m×0.25 mm×0.25 μm film thickness). Helium carrier gas was used at a constant flow rate of 1.0 mL/min.

The gas chromatograph oven was programmed at an initial temperature of 190° C. (hold for 1 minute) followed by a 3° C./minute ramp to 260° C. (hold for 10 minutes at 260° C.). The capillary column was interfaced directly to the mass spectrometer (Thermoquest GCQ ion trap), with the transfer line temperature at 260° C. Using this oven program, all compounds of interest were found to elute within 20 minutes.

The mass spectrometer ion source was maintained at 150° C. Spectra were recorded from m/z 50 to 500 using both electron impact mode (70 eV) and chemical ionization (CI) mode with ammonia reagent gas.

Retention times for the monosaccharides were established by derivatizing pure standards of individual sugars and/or chromatographing commercially available mixtures of alditol acetates (Supelco, Inc.). The sugars present in the sample extracts were identified by comparison of retention times and mass spectra against these standards. All samples with immunomodulatory activity contain glucose, galactose, rhamnose, mannose and arabinose. Extracts of molecular weight greater than $1 \times 10^6$ Da are substantially free of ribose.

(b) Monosaccharide Compositional Analysis Using Polyacrylamide Gel Electrophoresis (PAGE)

The standard hydrolysis protocols to release acidic, neutral or basic monosaccharides from the polysaccharide backbones were employed. The liberated monosaccharides were labeled with fluorescent labeling reagent 2-aminoacridone (AMAC) first, followed by reduction of the formed Schiff base with sodium cyanoborohydride. Polyacrylamide gel electrophoresis of the mixtures was then run on gradient gels according the instruction manual. Hydrolysates produced from IBP-2 contained glucose, galactose, rhamnose mannose, and arabinose. A substantial mount of ribose was also found. However, the hydrolysates produced by treatment of IBP-5 and IBP-7 with 2M TFA at 100° C. for 5 h clearly contained only glucose and galactose as well as rhamnose, mannose and arabinose. No ribose was found in these hydrolysates. This was in accord with our previous findings that RNA fragments of low molecular mass were present in IBP-2. However, because of their small size they could not be present in high molecular mass peaks of IBP-5 and IBP-7 obtained from Sephadex G 100 of Sephacryl S 300 chromatographies, respectively. Another band placed between N-acetyl galactosamine (GalNAc) and mannose was detected in PAGE but could not be assigned to any of the conventional monosaccharides. The reaction mixtures obtained by hydrolysis performed under the conditions used for sialic acid release (0.1 TFA, 80° C., 1 h) resulted in a product with a Rf identical with that of sialic acid and another major band with retention time significantly slower than that corresponding to GalNAc. Four molar HCl hydrolysis for 3 h at 100° C. (a condition for aminosugar release) resulted in PAGE in bands corresponding to GalNAc and N-acetyl glucosamine (GlcNAc). However judging from the intensity of other bands they were insignificant components of IBP-5 of IBP-7.

(c) Monosaccharide Compositional Analysis Using Capillary Electrophoresis(CE)

The protocol followed was that of Sato et al. (Sato K., Okubo A., Yamazaki T., (1997) Determination of monosaccharide derivatized with 2-aminobenzoic acid by capillary electrophoresis. Anal Biochem 251: 119–121). IBP-2 or its fractions were hydrolyzed first in 0.1 M TFA (1 mg/ml), at 100° C. for 18 h, the aqueous acid was removed under reduced pressure, the residual TFA was removed by a sequential evaporation with methanol until dryness.

Figure 14:
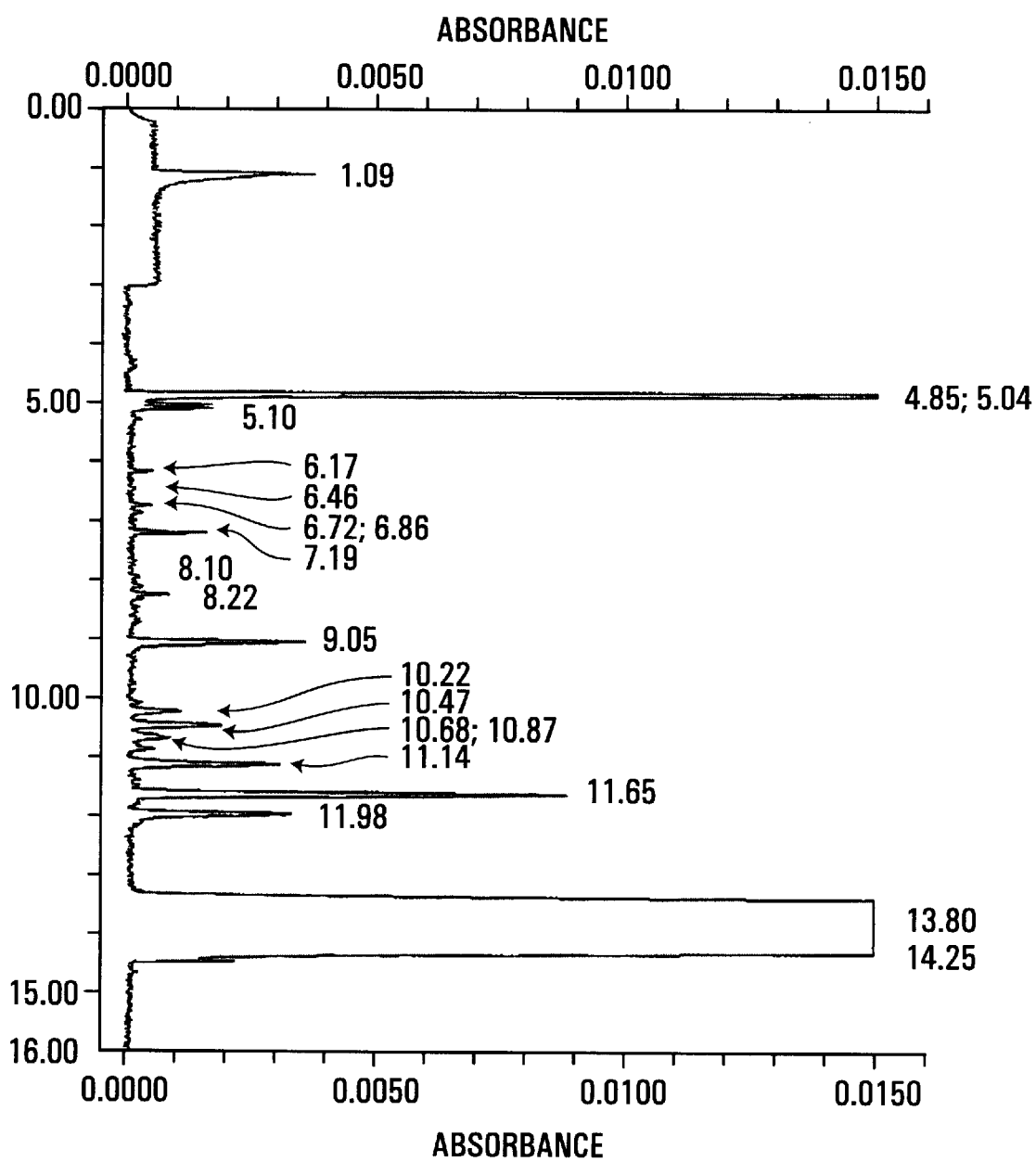
FIG. 14: Capillary electrophoresis chromatogram of the dialyzed crude extract IBP-2. The monosaccharides are assigned to the peaks as follows: ribose at position 9.05; rhamnose at position 10.47; mannose at position 10.68; galactose at position 11.14; and glucose at position 11.65.
Figure 15:
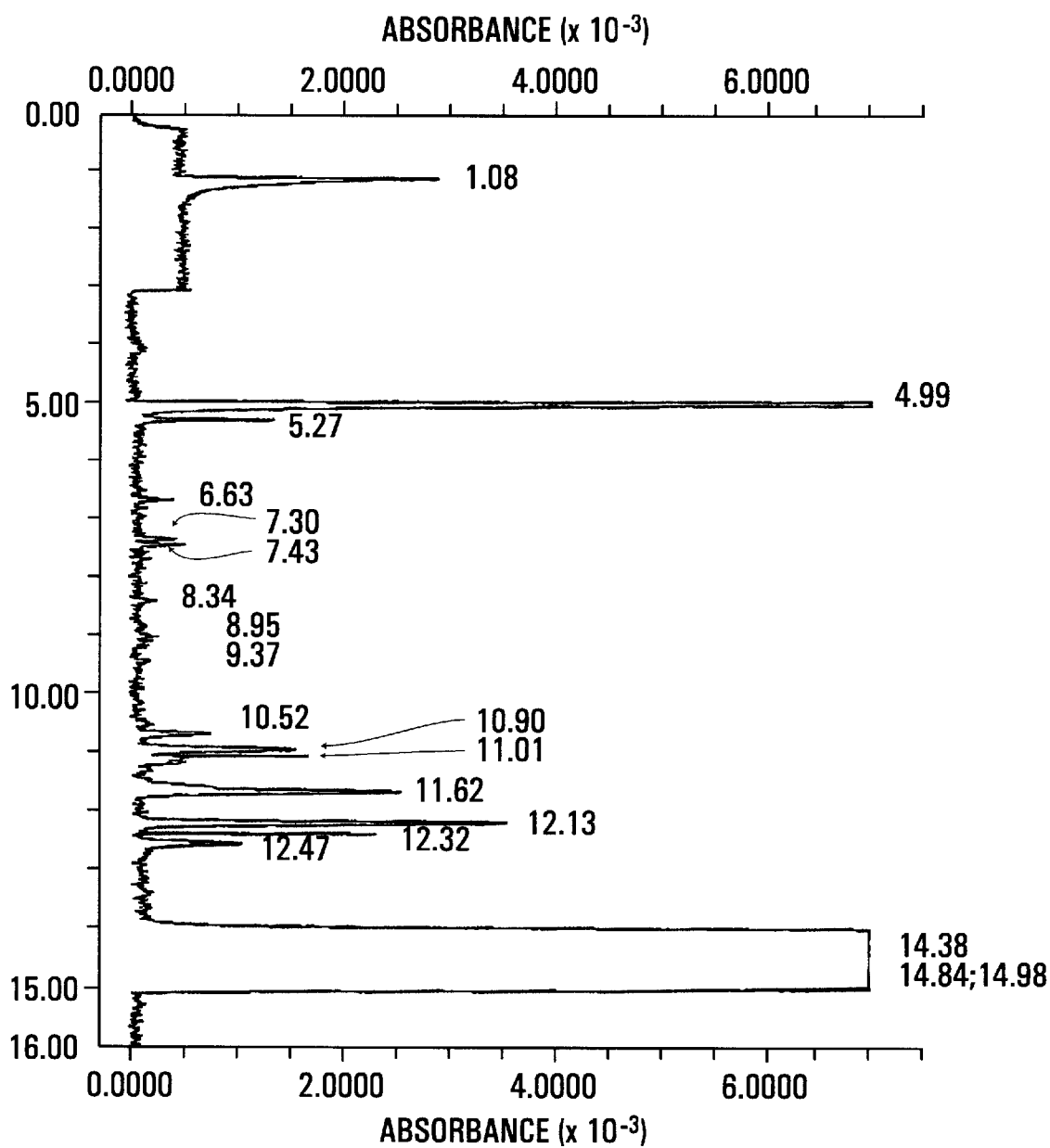
FIG. 15: Capillary electrophoresis chromatogram of the retained portion after IBP-2 was passed through a 1 MDa MWCO ultrafiltration membrane. The monosaccharides are assigned to the peaks as follows: N-acetyl galactosamine (GalNAc) at position 7.30; N-acetyl glucosamine (GlcNAc) at position 7.43; arabinose at position 10.52; rhamnose at position 10.90; mannose at position 11.11; (note that the peak at position 11.01 is a bubble; the mannose peak is just to the right of this peak); galactose at position 11.62; glucose at position 12.13.

The crude extract IBP-2 contains primarily glucose and galactose; glucose is the most prevalent monosaccharide in the extract. Also present are rhamnose, mannose and arabinose, albeit in significantly smaller quantities (FIG. 14). When the extract was subjected to ultrafiltration using a 1 Mda MWCO membrane (FIG. 15), the ratio between glucose and galactose changed and the ribose peak disappeared, indicating (in agreement with PAGE data) removal of RNA and its fragments.

(d) Amino Acid Composition

The free amino acids contained in the extracts were determined as follows: The samples were dissolved in distilled de-ionized water for a final concentration of 10 mg/mL. To 25 µL (250 µg) of each sample, 75 µL of Beckman sample buffer (Na-S) was added. Samples were centrifuged at 16,000×g to remove particulate matter before analysis on the Beckman Model 6300 amino acid analyser. The centrifugation clarified the solution and the pellet was retained; the supernatant was analysed for free amino acids.

To determine the amino acid composition of whole hydrolysates, portions of each sample (250 µg) were placed into a cleaned glass test tube along with the internal standard norleucine and 1 mL 6N HCl. The tubes were sealed under vacuum and the peptides and polypeptides hydrolysed at 105° C. for 20 hours. The tubes were opened and the samples were dried in a Savant Environmental Speed-vac at room temperature. The residues were re-dissolved in Na-S buffer and handled as described above for the determination of free amino acids.

(e) DNA Content

The Chlorella extract was dissolved in distilled water (500 E$\mu$). An equal volume of a phenol/chloroform/isoamyl alcohol (25:24:1, v/v) solution is added. The mixture is shaken vigorously then centrifuged at 13,000 rpm for 5 minutes. The top aqueous layer is pipetted off and re-extracted with an additional 500 µL of the organic mixture. The aqueous layer is re-extracted until the protein layer (a visible interface between the aqueous and organic layers) is negligible. After the final protein extraction, the aqueous layer was transferred to a fresh tube and to it was added glycogen (10 µL), 3M sodium acetate (50 µL), and cold ethanol (1 mL). The mixture was shaken and placed in the −80° C. freezer for an hour. It was then centrifuged at 13,000 rpm for 15 minutes and the supernatant was poured off. The pellet was dried on the speed-vacuuming and re-dissolved in water. Its absorbance was measured at 260 nm against a water blank. Since proteins also absorb at 260 nm, protein absorbance readings at 280 nm were also taken as a measure of protein content in the DNA sample.

EXAMPLE 7

Enzyme Digestion of Extracts

Enzyme degradation was used as a technique to selectively eliminate various macromolecular classes from the Chlorella extracts. IBP-2 or its fractions (both IBP-2 and its fractions are designated ONC-107 in this example) were treated with pronase, DNAse, RNAse, amylase, amyloglucosidase, cellulase and neuraminidase in separate experiments. SDS page and agarose electrophoresis as well as thin layer chromatography were used to monitor the enzymatic reactions (see sections (a) to (g) below). The final reaction mixtures were dialyzed, lyophilized and tested for the capacity to stimulate undifferentiated spleen cells by thymidine incorporation into murine splenocytes (Examples 9 and 11). The results are summarized as follows:

No effect on the capacity to stimulate undifferentiated spleen cells within a statistical significance after treatment with the selected enzymes.

No presence of large molecular mass RNA in IBP-2. This is in agreement with other findings (above), specifically that no ribose was found in high molecular mass species (IBP-5, IBP-7) and in fractions ultrafiltered with MWCO>1 MDa. This clearly demonstrates that RNA is not the primary source of the immunostimulating activity.

A very small quantity of DNA was found, which is in accord with our data obtained from the isolation of DNA using a silicon carbide column (about 2% content, 500 bp) (see Haj-Ahmad Y (1999) Nucleic acid purification and process. Canadian published application 2,270,106).

All enzyme digestions were performed in parallel with positive controls to ensure that the enzymes were active. The experiments clearly indicate that unassociated, enzyme-accessible protein and nucleic acids are unlikely to be sources of the activity. The source of immunoactivity is a polysaccharide (perhaps complexed with another biopolymer which has no significant effect by itself and which might have an indirect role, e.g. stability). The immunoactivity of the polysaccharide is not affected by cleavages in the regions of three or more α-1,4-linked D-glucose units, α-1,4-linked glucosides and galactosides, or α-1,4-linked D-glucose, assuming such linkages are accessible to enzyme cleavage.

(a) Protease Treatment

Protease (100 µg/ml, Streptomyces griseus) was added to ONC-107 (20 mg/ml) in TRIS buffer (0.05M, pH 7.4) and incubated for 1 hour at 36° C. Incubation was stopped by heat deactivation of the enzyme at 80° C. for 1 hour followed by centrifugation for 10 minutes at 13000 rpm. Aliquots were taken from the solution at time intervals of 0, 5, 10, 15, 30 and 60 minutes and prepared for analysis by SDS-PAGE electrophoresis (12% gel, total protein stain). The optimum concentration of protease was determined by a similar electrophoretic time course involving BSA (1 mg/ml). The final digest mixture was analyzed by agarose electrophoresis (1% stained with ethidium bromide).

(b) DNAse Treatment

DNAse (100 µg/ml) was added to ONC-107 (20 mg/ml) in TRIS buffer (0.05M, pH 7.4, 10 mM $MgCl_2$) and incubated for 1 hour at 36° C. Incubation was stopped by heat deactivation of the enzyme at 80° C. for 1 hour followed by centrifugation for 10 minutes at 13000 rpm. The final digest mixture was analyzed by SDS-PAGE electrophoresis (12% gel, total protein stain) to check for protein degradation. Agarose electrophoresis (1% stained with ethidium bromide) was used to confirm nucleic acid degradation.

(c) RNAse Treatment

RNAse (100 µg/ml) was added to ONC-7 (20 mg/ml) in TRIS buffer (0.05M, pH 7.4, 10 mM NaCl) and incubated for 1 hour at 36° C. Incubation was stopped by heat deactivation of the enzyme at 80° C. for 1 hour followed by centrifugation for 10 minutes at 13000 rpm. The final digest mixture was analyzed by SDS-PAGE electrophoresis (12% gel, total protein stain) to check for protein degradation. Agarose electrophoresis (1% stained with ethidium bromide) was used to confirm nucleic acid degradation.

(d) Amylase Treatment

Amylase (100 µg/ml) was added to ONC-7 (20 mg/ml) in TRIS buffer (0.05M, pH 7.4) and incubated for 1 hour at 36° C. Incubation was stopped by heat deactivation of the enzyme at 80° C. for 1 hour followed by centrifugation for 10 minutes at 13000 rpm. The final digest mixture was analyzed by SDS-PAGE electrophoresis (12% gel, total protein stain) to check for protein degradation. Agarose electrophoresis (1% stained with ethidium bromide) was used to confirm nucleic acid degradation.

Additionally, thin layer chromatography (TLC) confirmed the activity of the enzyme as follows. Amylase (100 µg/ml) was added to a solution of starch (1 mg/ml) and incubated for one hour at 36° C. The solution was analyzed via TLC using keisgel silica plates eluted with isopropanol:ethylacetate:water (7:1:2). The plates were developed after 10 minutes drying in the horizontal position using a sulfuric acid/ethanol solution. Glucose (1 mg/ml) was used as a control as was untreated starch. Treatment of starch with amylase resulted in the liberation of glucose.

(e) Amyloglucosidase

Amyloglucosidase (100 µg/ml) was added to ONC-7 (20 mg/ml) in TRIS buffer (0.05M, pH 4.4) and incubated for 1 hour at 36° C. Incubation was stopped by heat deactivation of the enzyme at 80° C. for 1 hour followed by centrifugation for 10 minutes at 13000 rpm. TLC confirmed the activity of the enzyme as follows. Amyloglucosidase (10 µg/ml) was added to a solution of starch (1 mg/ml) and incubated for one hour at 36° C. The solution was analyzed via TLC using keisgel silica plates eluted with isopropanol:ethylacetate:water (7:1:2). The plates were developed after 10 minutes drying in the horizontal position using a sulfuric acid/ethanol solution. Glucose (1 mg/ml) was used as a control as was untreated starch. Treatment of starch with the amyloglucosidase resulted in the liberation of glucose.

(f) Cellulase

Cellulase (100 µg/ml) was added to ONC-7 (20 mg/ml) in TRIS buffer (0.05M, pH 7.4) and incubated for 1 hour at 36° C. Incubation was stopped by heat deactivation of the enzyme at 80° C. for 1 hour followed by centrifugation for 10 minutes at 13000 rpm. TLC confirmed the activity of the enzyme as follows. Cellulase (100 µg/ml) was added to a solution of cellulose (1 mg/ml) and incubated for one hour at 36° C. The solution was analyzed via TLC using keisgel silica plates eluted with isopropanol:ethylacetate:water (7:1:2). The plates were developed after 10 minutes drying in the horizontal position using a sulfuric acid/ethanol solution. Glucose (1 mg/ml) was used as a control as was untreated cellulose. Treatment of cellulose with cellulase resulted in the liberation of glucose.

(g) Neurominidase

Neurominidase (100 µg/ml) was added to ONC-7 (20 mg/ml) in TRIS buffer (0.05M, pH 5.0) and incubated for 1 hour at 36° C. Incubation was stopped by heat deactivation of the enzyme at 80° C. for 1 hour followed by centrifugation for 10 minutes at 13000 rpm. TLC confirmed the activity of the enzyme as follows. Neurominidase (100 µg/ml) was added to a solution of N-acetyl-neuromidose (1 mg/ml) and incubated for one hour at 36° C. The solution was analyzed via TLC using keisgel silica plates eluted with isopropanol:ethylacetate:water (7:1:2). The plates were developed after 10 minutes drying in the horizontal position using a sulfuric acid/ethanol solution.

EXAMPLE 8

Stimulation of Splenocyte Proliferation

Figure 7:
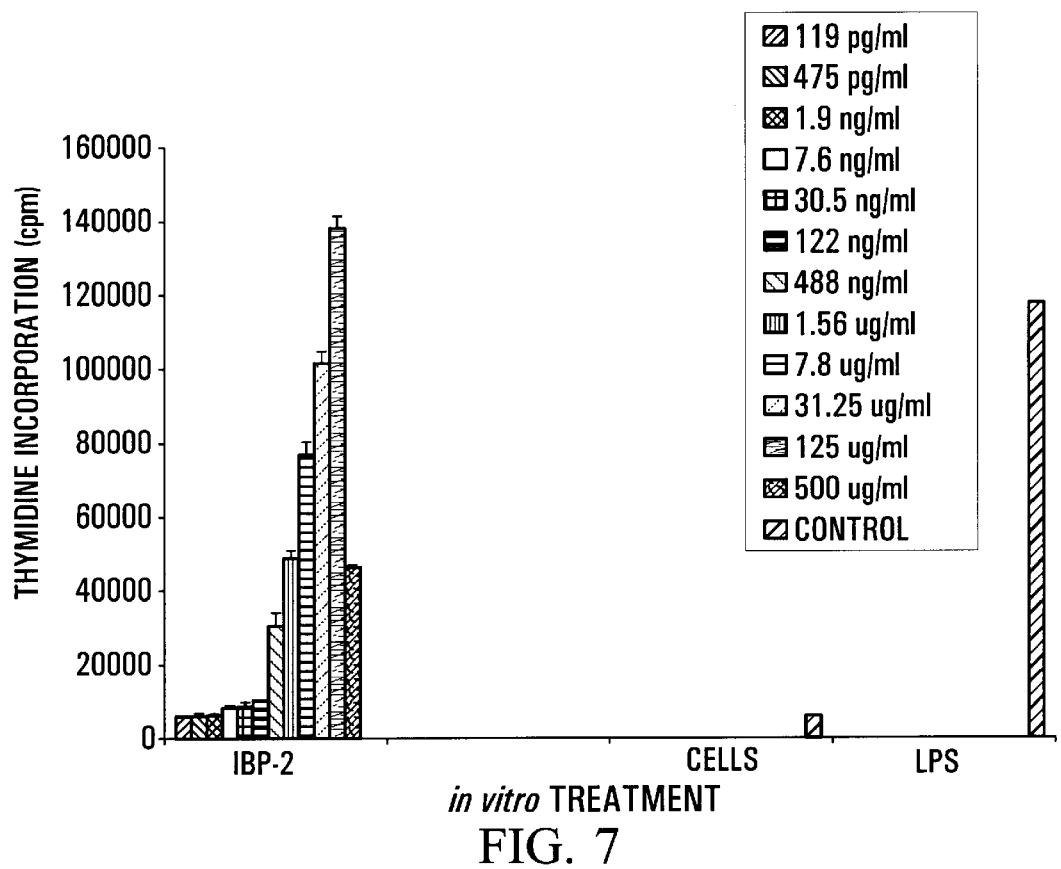
FIG. 7: Splenocyte proliferation—Titration curve of IBP-2; 'Cells' is a negative control; LPS is a positive control.
Figure 13:
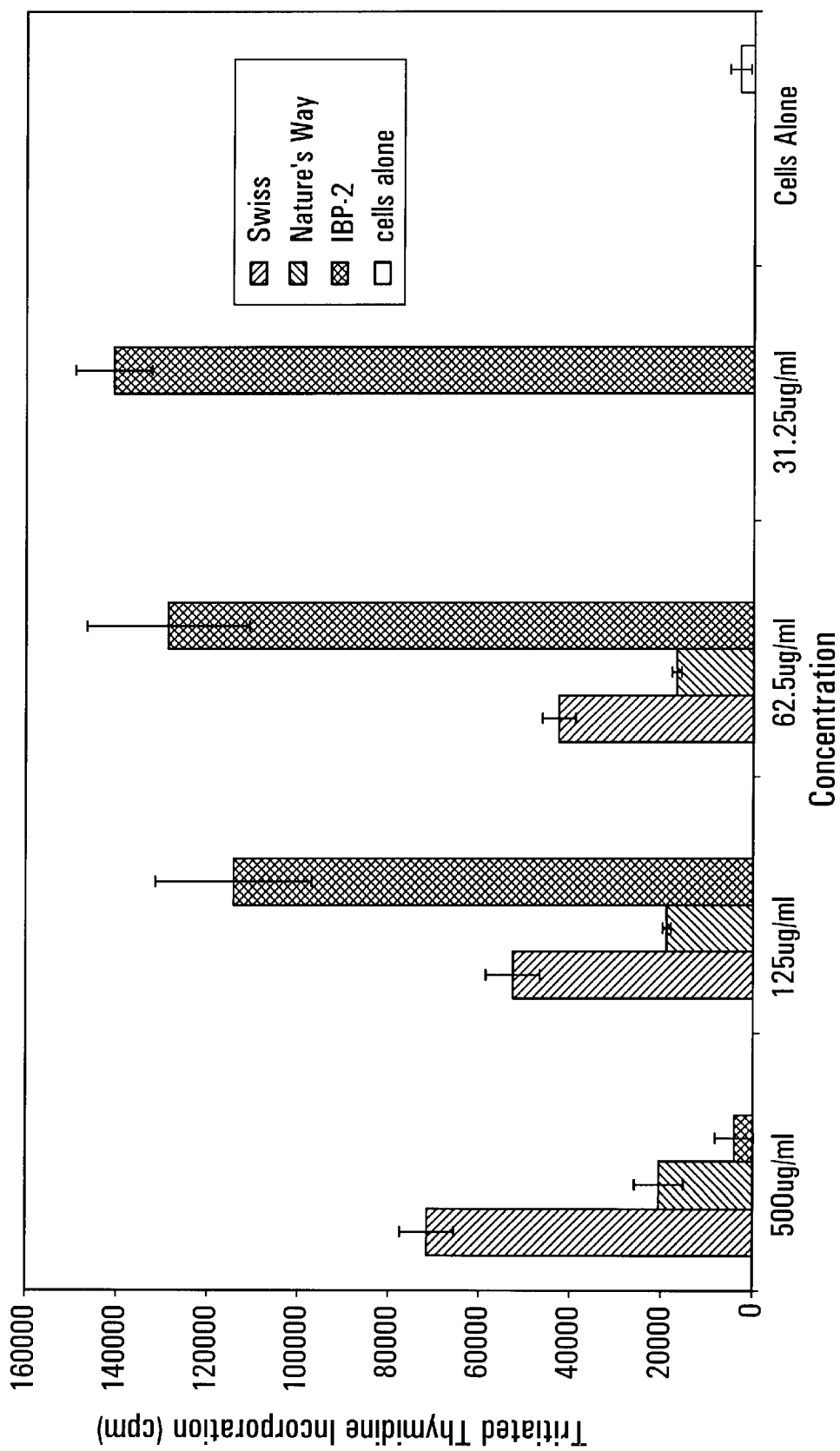
FIG. 13: Mouse splenocyte proliferation as measured by $^3$H-incorporation, cultured in the presence of IBP-2 or commercial Chlorella extracts from Swiss Herbal and Nature's Way.

Fresh splenocyte cells (splenocyte primary culture) were plated at $3 \times 10^5$ cells/well in cRPMI medium in a 100 µl volume in 96-well flat bottom tissue culture plates. Test samples in 100 µl of cell medium were added to triplicate wells giving a final total volume in each well of 200 µl. The plates were covered with sterile lids and incubated in 5% $CO_2$ at 37° C. and 100% humidity in a $CO_2$ incubator for 48 h. The cells were then pulsed with $^3$H-thymidine (1 µCi per well in 10 µl cRPMI) and incubated for 18 h. Cells were harvested with an automated cell harvester equipped with filter strips. The filter strips were allowed to dry for 3 h at 37° C. The radioactivity incorporated by the cells was determined by counting the filter strips immersed in scintillation medium in a liquid scintillation counter. An example of the experiment is illustrated in FIG. 7. A comparison of applicant's extract with two commercial samples is illustrated in FIG. 13.

EXAMPLE 9

Isolation of B-cells and T-cell from Splenocytes and Stimulation of the Cells

Mouse splenocytes were isolated by routine methods and placed in tissue culture flasks at 37° C. for 2 hr, to allow the macrophages to settle and adhere to the flask. The lymphocytes (which are suspended and do not adhere) are then removed and placed in a 50 ml centrifuge tube, spun and resuspended in a small amount of cold PBS-EDTA-BSA buffer (pH 7.4; 1–3 ml) and placed on ice. Cells were counted and recentrifuged. They were then resuspended at $1 \times 10^8$ in 0.3 ml of the PBS-EDTA-BSA buffer in a 15 ml centrifuge tube.

Negative isolation of B-cells: 100 µl of Miltenyi microbeads coated with anti-Thy-1.2 antibody was added to the resuspended cells, and the mixture was incubated for 20 minutes. PBS-EDTA-BSA (5 mL) was added and the suspension was pipetted into a midiMACS column in a midiMACS magnet. The column had a 25-gauge needle on the outflow to restrict the flow rate. The T-cells, bound to the anti-Thy-1.2 antibody-coated magnetic beads, adhered to the column. The B-cells passed through and were collected. The column, without being removed from the magnet, was rinsed with 5 ml of the buffer to remove any residual B-cells. The B-cells were combined, spun, resuspended in 1 ml of cRPMI and counted. They were then resuspended to $5 \times 10^6$ cells per ml of cRPMI and plated at 100 µl/well for stimulation assays.

Negative isolation of T-cells: The same procedure was followed as for isolation of B-cells, except the magnetic beads used for the incubation were coated with anti-B220 antibody instead of anti-Thy-1.2.

Figure 8:
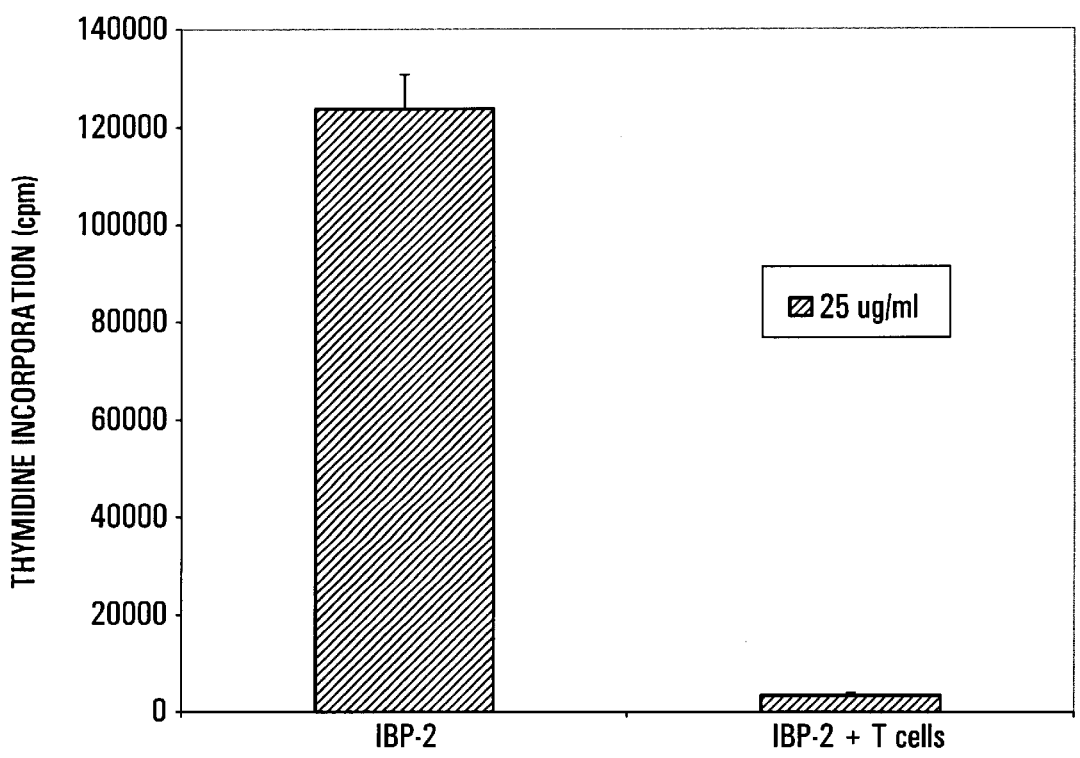
FIG. 8: Proliferation assay measuring $^3$H-incorporation by isolated B- or T-cells in the presence of 25 μg/mL IBP-2.

The purified T- and B-cell populations were tested as described in Example 8. The results are shown in FIG. 8.

EXAMPLE 10

Nitrite Assay for Mouse Peritoneal Macrophages

Mice were euthanized by cervical dislocation, and placed spreadeagled on their backs. Their abdomens were sterilized with 70% alcohol, and a careful midline incision exposing the INTACT peritoneal wall was made. A 10 -ml syringe was used to inject 10 ml of cold cRPMI-1640 into the mouse peritoneal cavity. The mice were gently rocked from side to side with the needle still inserted. The cRPMI-1640 containing the peritoneal macrophages was slowly drawn from the peritoneal cavity through the needle. About 8 ml of fluid per mouse was recovered. The peritoneal fluid was pooled and put into 50 mL centrifuge tubes on ice. The cells were spun down, washed and resuspended in 1 ml of cRPMI-1640. After counting, they were resuspended to $1-2 \times 10^6$ cells/ml and plated into a 96-well tissue culture plate at $1 \times 10^5$ cells/well in a 100 μl volume. Test samples were added in cRPMI (100 μl) with and without IFN-μ. The positive controls were the cells+IFN-μ and LPS+IFN-μ. The cells were incubated for 48 h in a $CO_2$ incubator in 5% $CO_2$.

Figure 9:
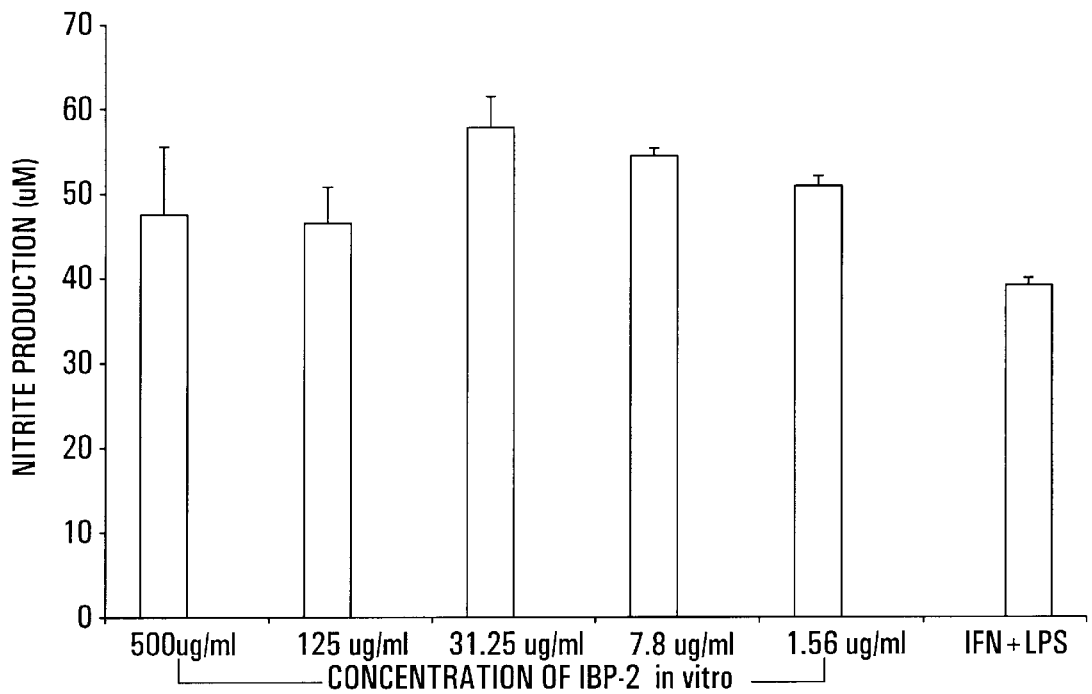
FIG. 9: Nitric oxide production by BALB/c inflammatory peritoneal macrophages cultured in the presence of various concentrations of IBP-2; 'IFN+LPS' is a positive control.

Fifty μl of the culture fluid was collected and transferred to wells in a 96-well flat bottom ELISA plate. Twofold serial dilutions of $NaNO_2$ (125 μM to 1 μM final concentration) in cRPMI were made, and 50 μl of each Greiss Reagent solution and the $NaNO_2$ dilutions were added to a set of wells to provide a standard curve. Absorbance at 550 nm was measured and a plot of absorbance values against $NaNO_2$ concentrations was made. The standard curve was used to determine the amount of $NO_2^-$ produced by the peritoneal macrophage samples. An example of the experiment is illustrated in FIG. 9.

EXAMPLE 11

Determination by Sandwich ELISA of Stimulation of Cytokine Production by Mouse Splenocytes Cytokine production was measured in mouse splenocytes, in separated mouse T- and B-lymphocytes, and in mouse macrophages. The test samples were added at several concentrations to the cells in microtiter tissue culture plates. After incubating for 24–48 h, depending on the cytokine of interest, the supernatant culture fluid was removed for ELISA.

ELISA plates were coated with anti-cytokine monoclonal antibodies by incubation at 4° C. overnight in a carbonate buffer, pH 9.6. The plates were then washed with Tris-buffered saline (TBS), post-coated with 2 mg/ml BSA in TBS, (200 μl/well) for 2 h at room temperature and washed with TBS/Tween. The samples and standards (the latter diluted 1 ng/ml to 15 μg/ml in twofold dilutions) were diluted in TBS/Tween containing 1 mg/ml BSA (100 μl/well), added to the plate, incubated overnight at 4° C. and then washed with TBS-Tween.

Figure 10:
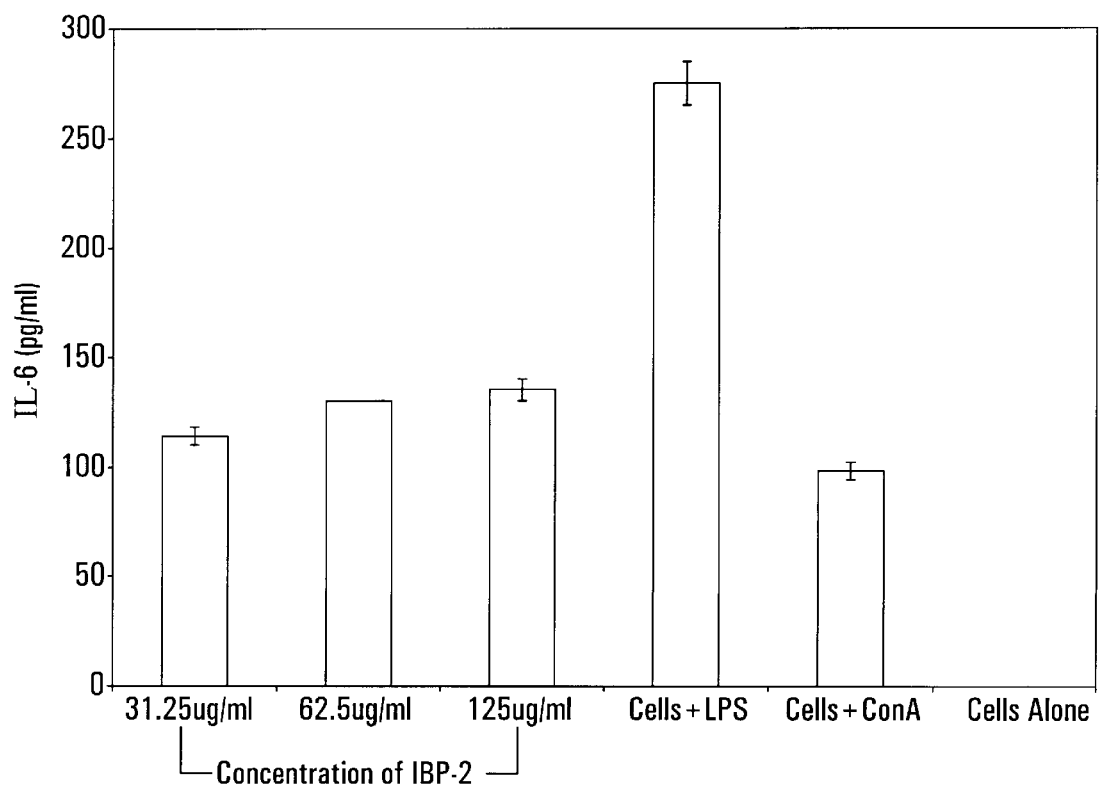
FIG. 10: IL-6 production by BALB/c mouse spleen cells in the presence of various concentrations of IBP-2; 'Con A' is Concanavalin A; 'Cells+ConA' and 'Cells+LPS' are positive control samples, Concanavalin A is at 10 μg/mL; LPS is at 20 μg/mL.

The appropriate biotinylated anti-cytokine mAb (0.5 μg/ml) in PBS-Tween containing 1 mg/ml BSA (100 μl/well), was added. The plate was incubated at room temperature for 1 h and then washed with TBS-Tween. Extravidin-Peroxidase in PBS-Tween containing 1 mg/ml BSA (100 μl/well) was added and incubated at room temperature for 30 minutes. The plates were then washed. One hundred μl/well of TMB substrate solution was added, and after 10 to 30 minutes, depending on color development, the reaction was stopped with 100 μl/well of 1 M $H_3PO_4$. The plate was read at 450 nm. An example of stimulation of IL-6 production is illustrated in FIG. 10.

EXAMPLE 12

Effect of IBP-2 on Proliferation of *Listeria Monocytogenes* in Infected Mice

Figure 11:
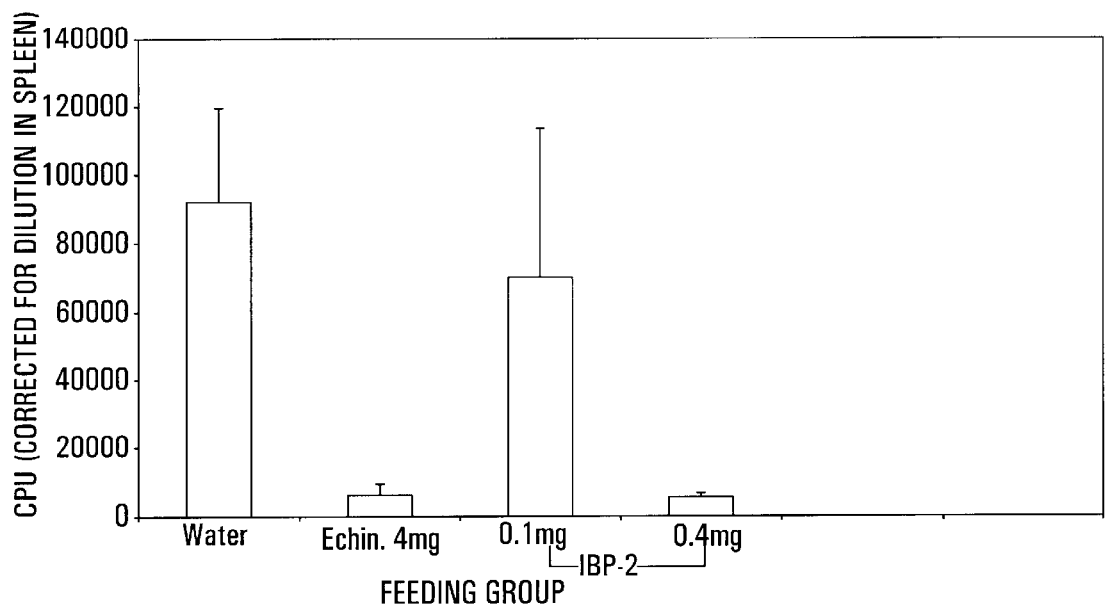
FIG. 11: Effect of IBP-2 compared to 4 mg echinacea (Echin.) on *Listeria monocytogenes* proliferation in mice.

Two doses of IBP-2 (0.1 mg or 4 mg) or plain water (negative control) were administered to Balb/c mice by intragastric tube three times a week for four weeks. The mice were then infected by intravenous injection of 5,000 viable *Listeria monocytogenes* organisms. Three days after the Listeria injections, the mice were sacrificed. Cell suspensions of their spleens were made and cultured on culture dishes to determine the number of bacteria in the spleens. The water-fed animals had 92,202 (±23,000) bacterial colony forming units (CFUs) in their spleens; (the number in bracket refers to the standard deviation). The animals fed 0.1 mg of IBP-2 per dose had 43,310 (±7,021) CFUs and the animals fed 4 mg of IBP-2 per dose had only 5,317 (±492) CFUs ($p<0.05$) (FIG. 11).

EXAMPLE 13

Effect of IBP-2 on Proliferation of *Candida Albicans* in Infected Mice

Figure 12:
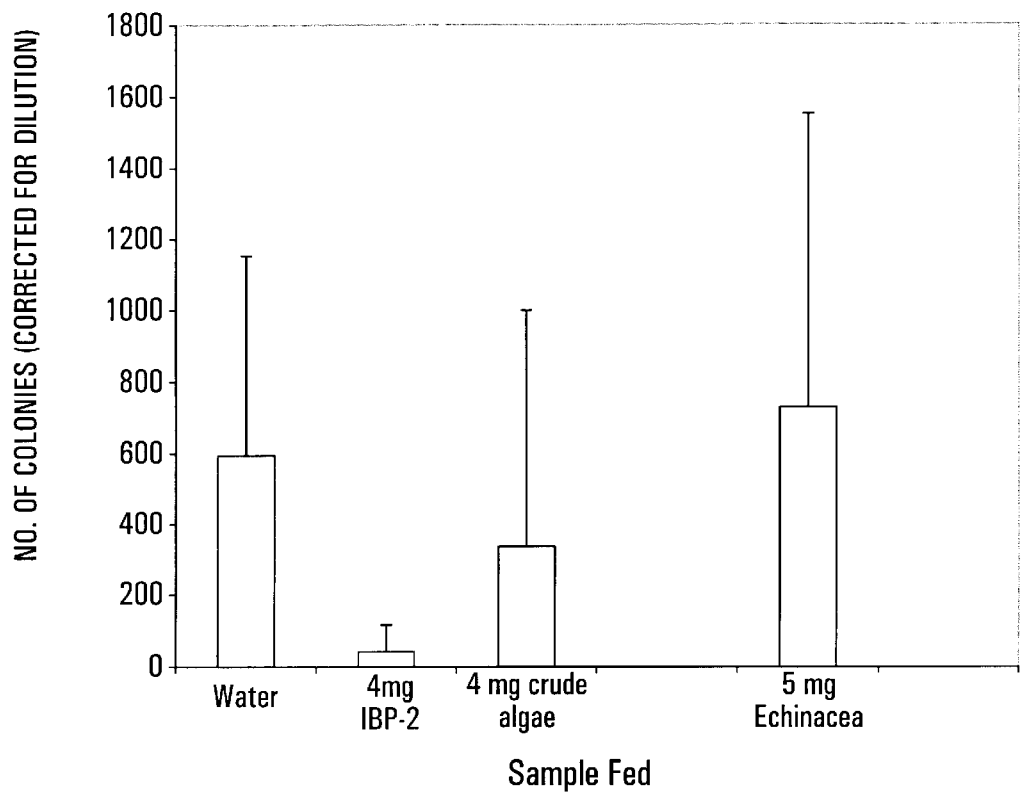
FIG. 12: Effect of IBP-2 compared to crude algae and echinacea on *Candida albicans* proliferation in mice.

IBP-2 (4 mg), crude algae (4 mg or 20 mg), or plain water was administered to Balb/c mice by intragastric tube 3 times per week for two weeks. The mice were then infected by intravenous injection of 500,000 viable *Candida albicans* organisms. Feeding continued until the mice were sacrificed 12 days after infection. The kidneys were removed and cell suspensions made and cultured on Sabouraud agar to determine the number of *C. albicans* colonies which developed overnight. The following results were obtained: water fed mice 594 (±556) colonies (mean±standard deviation); IBP-2 (4 mg) fed mice 42 (±75) ($p<0.05$ compared to water fed mice); algae (4 mg) fed mice 335 (±663); algae (20 mg) fed mice 79 (±70); (statistically, the p value for this group compared to the water fed group was >0.05, although it was very close to being significant). The results are illustrated in FIG. 12.

EXAMPLE 14

Phase 2 Clinical Trial Study

This study was designed to assess the immunostimulatory efficacy of Chlorella extracts as a nutritional supplement in healthy adults over 50 years of age. A first-in-man study was completed which demonstrated the safety and tolerability of a Chlorella extract corresponding to IBP-1 when given as a once daily supplement over three weeks. This purpose of this phase 2 study was to increase the human experience with Chlorella extracts through increased safety and tolerability assessment and to explore the capacity of Chlorella extracts as an immune stimulating nutritional supplement in humans.

The study was designed as a randomized, placebo controlled clinical trial in which adults 50 years of age or older were assigned by chance to receive a 200 mg capsule of a Chlorella extract corresponding to IBP-1, (designated ONC-7 for the purpose of this study), a 400 mg capsule of ONC-7, or a placebo capsule (containing no ONC-7). While the trial was underway, the investigators, the nurses and other study personnel and the participants were not aware to which group they were assigned. The safety and side effects were measured by careful recording by the participant of any adverse event and reporting these to study personnel. Specific adverse events measured included fever, abdominal pain, nausea, vomiting, diarrhea, fatigue, decreased appetite, headache, body aches, sore joints, and rash. Safety was also measured by a series of blood tests before starting the study capsules and at the completion of the study capsules. These tests included tests of liver function (AST, ALT), blood profiles (complete blood count), and immunological function (ANA, anti-DNA, rheumatoid factor, Coombs, C3, C4, quantitative IgG, IgA, IgM, and IgE). Medication was taken for 28 days; after 21 days, participants were immunized with a commercially available, inactivated, split virion influenza vaccine. Antibody response to the immunization was assessed by measuring antibodies to the three influenza virus strains before, and 7 and 21 days after immunization. Cell mediated immunity was measured by evaluating the response to an influenza skin test at the beginning of the study and one week after the immunization.

A total of 124 subjects were enrolled into the study and took the study medication; 7 participants withdrew from the study. Only one participant withdrew because of adverse events (nausea and abdominal pain). The three treatment groups were similar in age, gender and baseline history and physical examination at the commencement of the study. The majority of participants were women (73.2–80.5% of each group). Participant compliance was excellent. Antibody response to the influenza vaccine was not significantly higher in the ONC-7 treated participants overall although in participants 55 years of age or younger there was a significantly enhanced response to some antibody measures (and a consistent trend to the others). There were no serious adverse events in any of the study participants. An adverse event was reported by most participants at sometime during the study but, for the most part, these events were not reported more frequently in the ONC-7 recipients compared to the placebo recipients (fatigue was reported more frequently by 200 mg ONC-7 recipients and abdominal pain more frequently by placebo recipients older than 55 years of age). There were no significant changes in laboratory measurements before and after therapy, or between recipients of the ONC-7 and placebo.

The results of this phase 2 study of the nutritional supplement ONC-7 at doses of 200 mg and 400 mg for 28 days in healthy adults are outlined below. They indicate that, despite an age effect, this product is well tolerated and safe for oral administration and has a measurable immunostimulatory effect.

The immunostimulatory effect was measured by antibody response to influenza vaccine in healthy adults over 50 years of age, although these responses were in general limited to the younger cohort in the study population (50–55 years of age). The increase in antibody response in this subgroup was statistically significant for some of the comparisons but the trend was apparent in all serological comparisons made. The pre-study hypothesis that the effect of ONC-7 would be best observed in the older subjects because of their decreased responsiveness to influenza vaccine was not supported by the data; in contrast, it was the younger, more responsive subjects who demonstrated an effect of the ONC-7.

The younger subjects tended to show immunostimulatory effects of ONC-7 (especially 400 mg dose). A potential reason for the lack of effect in the older age group was that the older group may have had higher pre-immunization antibody titers which may indicate a greater degree of prior exposure to antigenically similar flu virus A strains (but not the B strains).

1. For the A/Caledonia strain of the flu vaccine, the younger (<=55 yrs.) age group had higher mean antibody titers with both doses than placebo at both 7 (not significant at 7 d) and 21 days (p=0.05): placebo=43.2; 200 mg=84.3; 400 mg=84.4.
2. For the B/Yamanashi strain of the flu vaccine, the 400 mg group had higher titers (30.1) at 7 days vs. placebo (14.4, p=0.03), but this was not significant at 21 days. The 200 mg dose was not significantly greater than placebo at 7 days (15.9) or 21 days (25.3).
3. For A/Panama strain of the flu vaccine, there was a similar trend in favour of 400 mg dose, but it was not significant. At 7 days, the 400 mg group had titers of 64.5, compared to placebo (39.9), which is not significant. The 200 mg group has titers of 26.6. At 21 days, there was also a trend in favour of 400 mg vs. placebo; again, 200 mg was not better than placebo (57.4).

Similar trends were observed for the proportion of subjects having 2- and 4-fold antibody responses.

For the B/Yamanashi in the <55 yr. group, only 5% of the placebo had a 2-fold antibody response at 7 days. This is in contrast with the 400 mg group (41.2%, p=0.01) and 200 mg group (6.3%, p=0.04).

There was also a non-significant trend for an increased response at 21 days, and a non-significant trend in the proportion of the <55 yr. age group achieving seroprotective levels of 40 RD (reciprocal dilutions) at 7 days post-immunization.

Numerous modifications, variations and adaptations may be made to the particular embodiments of the invention described above without departing from the scope of the invention which is defined in the claims.

What is claimed is:

1. A fraction having immunomodulating activity obtained by size fractionation of an extract of Chlorella, said fraction consisting essentially of high molecular weight polysaccharides and polysaccharide complexes having a molecular weight of about $4 \times 10^6$ Da to about $1 \times 10^7$ Da wherein said high molecular weight polysaccharides and polysaccharide complexes are at least 22% (w/w) of total Chlorella-derived content of the fraction.

2. The fraction of claim 1 wherein the high molecular weight polysaccharide and polysaccharide complexes are at least 26% (w/w) of the total Chlorella-derived content of the fraction.

3. The fraction of claim 1 wherein the high molecular weight polysaccharide and polysaccharide complexes are at least 30% (w/w) of the total Chlorella-derived content of the fraction.

4. The fraction of claim 1 wherein the high molecular weight polysaccharides and polysaccharide complexes are formed of glucose and at least one monosaccharide selected from the group consisting of galactose, rhamnose, mannose and arabinose.

5. The fraction of claim 4 wherein the high molecular weight polysaccharides and polysaccharide complexes are substantially free of ribose.

6. The fraction of claim 1 which is substantially free of nucleic acids and ribonucleic acids.

7. The fraction of claim 4 wherein the high molecular weight polysaccharides and polysaccharide complexes contain N-acetyl glucosamine and N-acetyl galactosamine.

8. The fraction of claim 1 which is substantially free of unassociated proteins.

9. The fraction of claim 1 which retains immunomodulating activity upon treatment under conditions and for a length of time sufficient to effect digestion of unassociated DNA.

10. The fraction of claim 1 which retains immunomodulating activity upon treatment under conditions and for a length of time sufficient to effect digestion of unassociated RNA.

11. The fraction of claim 1 which retains immunomodulating activity upon treatment under conditions and for a length of time sufficient to effect digestion of unassociated proteins.

12. The fraction of claim 1 which retains immunomodulating activity upon treatment under conditions and for a length of time sufficient to effect cleavage of glycosidic linkages with at least one glycosidase selected from the group consisting of amylase, amyloglucosidase, cellulase and neuraminidase.

13. The fraction of claim 1 which retains immunomodulating activity upon treatment under conditions and for a length of time sufficient to effect cleavage of:

(i) three or more α-1,4-linked D-glucose units;

(ii) α-1,4-linked glucosides;

(iii) α-1,4-linked galactosides; or (iv) α-1,4-linked D-glucose.

14. The fraction of claim 11 wherein the treatment is digestion with protease.

15. The fraction of claim 1 wherein the high molecular weight Chlorella polysaccharides and polysaccharide complexes are from *Chlorella pyrenoidosa*.

16. A pharmaceutical composition comprising the fraction of claim 1, in admixture with a pharmaceutically acceptable diluent or carrier.

17. A nutritional composition comprising the fraction of claim 1, and at least one energy source selected from the group consisting of carbohydrate, fat and nitrogen sources.

18. A nutritional supplement comprising the fraction of claim 1 and a supplement selected from the group consisting of vitamin E, vitamin C and folic acid.

19. A nutritional supplement comprising the fraction of claim 1 and a nutraceutical selected from the group consisting of fish oils, spirulina and echinacea.

20. A commercial package containing as an active ingredient the fraction of claim 1, together with instructions for its use as an immunomodulator.

21. A preparation comprising the fraction of claim 1 wherein the preparation is free of low molecular weight Chlorella polysaccharides and polysaccharide complexes of less than $4 \times 10^6$ Da.

22. The fraction of claim 1 wherein the high molecular weight polysaccharides and polysaccharide complexes are about $4 \times 10^6$ Da to about $5 \times 10^6$ Da.

23. The fraction of claim 1 wherein the high molecular weight polysaccharides and polysaccharide complexes are about $5 \times 10^6$ Da to about $7 \times 10^6$ Da.

24. The fraction of claim 1 wherein the high molecular weight polysaccharides and polysaccharide complexes are about $7 \times 10^6$ Da to about $9 \times 10^6$ Da.

25. The fraction of claim 1 wherein the high molecular weight polysaccharides and polysaccharide complexes are about $9 \times 10^6$ Da to about $1 \times 10^7$ Da.

* * * * *